(12) United States Patent
Ben Mocha et al.

(10) Patent No.: US 11,234,733 B2
(45) Date of Patent: Feb. 1, 2022

(54) CANNULA FOR USE IN INTRAOSSEOUS INJECTIONS

(71) Applicant: WAISMED LTD., Rosh Ha'Ayin (IL)

(72) Inventors: Moshe Ben Mocha, Tel Aviv (IL); Einat Swisa, Avihayil (IL)

(73) Assignee: WAISMED LTD., Rosh Ha'Ayin (IL)

( * ) Notice: Subject to any disclaimer, the term of this patent is extended or adjusted under 35 U.S.C. 154(b) by 155 days.

(21) Appl. No.: 16/294,327

(22) Filed: Mar. 6, 2019

(65) Prior Publication Data
US 2019/0201053 A1  Jul. 4, 2019

Related U.S. Application Data

(63) Continuation-in-part of application No. PCT/IL2017/051001, filed on Sep. 6, 2017.

(30) Foreign Application Priority Data

Sep. 7, 2016 (IL) .......................................... 247684

(51) Int. Cl.
| | | |
|---|---|---|
| *A61B 17/34* | (2006.01) | |
| *A61M 5/46* | (2006.01) | |
| *A61B 90/00* | (2016.01) | |

(52) U.S. Cl.
CPC .......... *A61B 17/3472* (2013.01); *A61B 90/06* (2016.02); *A61M 5/46* (2013.01);
(Continued)

(58) Field of Classification Search
CPC ......... A61B 90/00; A61B 90/06; A61B 17/34; A61B 17/3472; A61M 5/46
See application file for complete search history.

(56) References Cited

U.S. PATENT DOCUMENTS

| | | |
|---|---|---|
| 5,575,804 A | 11/1996 | Yoon |
| 7,201,722 B2 | 4/2007 | Krueger |
| (Continued) | | |

FOREIGN PATENT DOCUMENTS

| | | |
|---|---|---|
| EP | 2289433 A2 | 3/2011 |
| WO | 2015/196085 A | 12/2015 |

OTHER PUBLICATIONS

Written Opinion of the International Searching Authority for PCT/IL2017/051001, dated Dec. 10, 2017—5 pages.
(Continued)

*Primary Examiner* — Christopher J Beccia
(74) *Attorney, Agent, or Firm* — Corner Counsel, LLC

(57) ABSTRACT

A cannula for use in a terminable intraosseous device comprises a cannula body, and a penetrator-independent proximal bone penetration indicator (PBPI) associated with the body for positively indicating initial penetration into the proximal bone. In various embodiments, the PBPI comprises a roughened surface provided at a distal end of the cannula body to assist in increasing an amplitude of vibrations that are generated immediately upon contact with a proximal bone cortex during performance of an intraosseous injection, a resilient element fixed at one end which becomes plastically deformed, a visually indicative element which is exposed when the distance between the cannula body and penetrator is changed, or a frictionally engageable element. In some embodiments, a stopper prevents additional penetration into the proximal bone, and a reinforcing member inserted within a cannula body lumen reinforces a thin-walled portion of the cannula body.

22 Claims, 25 Drawing Sheets

(52) U.S. Cl.
CPC . *A61B 2017/348* (2013.01); *A61B 2017/3492* (2013.01); *A61B 2090/062* (2016.02)

(56) References Cited

U.S. PATENT DOCUMENTS

| | | | | |
|---|---|---|---|---|
| 8,419,683 | B2* | 4/2013 | Miller | A61B 10/025 604/117 |
| 9,956,114 | B2* | 5/2018 | Andino | A61M 5/3286 |
| 2003/0236506 | A1* | 12/2003 | Schofield | A61B 10/025 604/272 |
| 2004/0077973 | A1 | 4/2004 | Groenke et al. | |
| 2007/0066987 | A1 | 3/2007 | Scanlan et al. | |
| 2009/0204024 | A1* | 8/2009 | Miller | A61B 17/3472 600/567 |
| 2010/0004626 | A1* | 1/2010 | Miller | A61B 10/025 604/506 |
| 2011/0152866 | A1 | 6/2011 | Knutson | |
| 2013/0013154 | A1 | 1/2013 | Aoki | |
| 2013/0131545 | A1 | 5/2013 | Azimpoor et al. | |
| 2016/0022312 | A1* | 1/2016 | Tang | A61B 17/3474 604/506 |
| 2017/0095369 | A1* | 4/2017 | Andino | A61M 5/329 |

OTHER PUBLICATIONS

International Preliminary Report on Patentability for PCT/IL2017/051001, dated Jan. 21, 2019—20 pages.
International Search Report for PCT/IL2017/051001, dated Dec. 10, 2017—11 pages.
Unimed SA Medical Needles Catalog No. 2008-A, p. 39 (appears to have been published in 2001) (51 pages).
Communication and Supplementary European Search Report for EP 17 84 8283; dated Mar. 18, 2020 (8 pages).

* cited by examiner

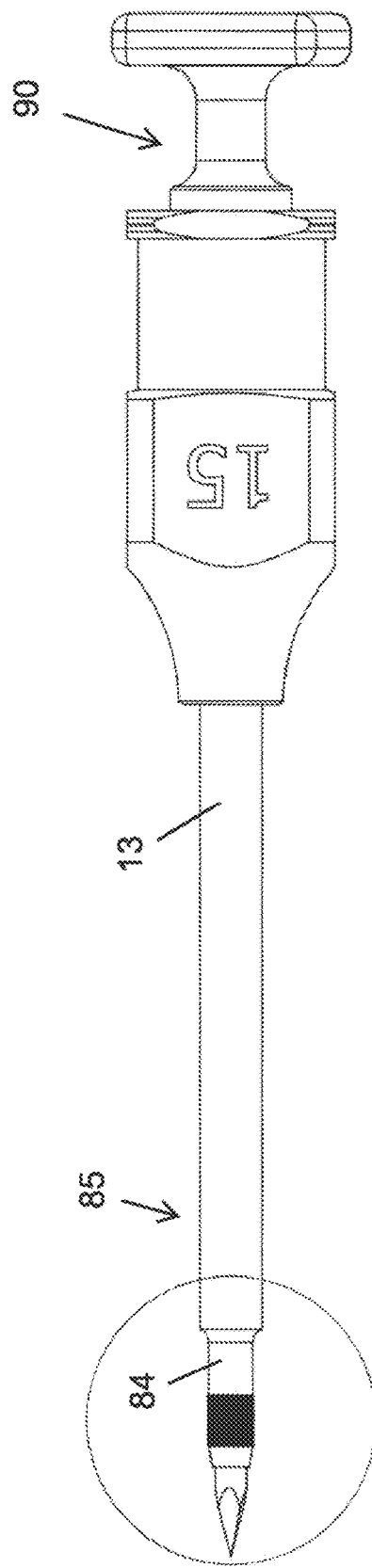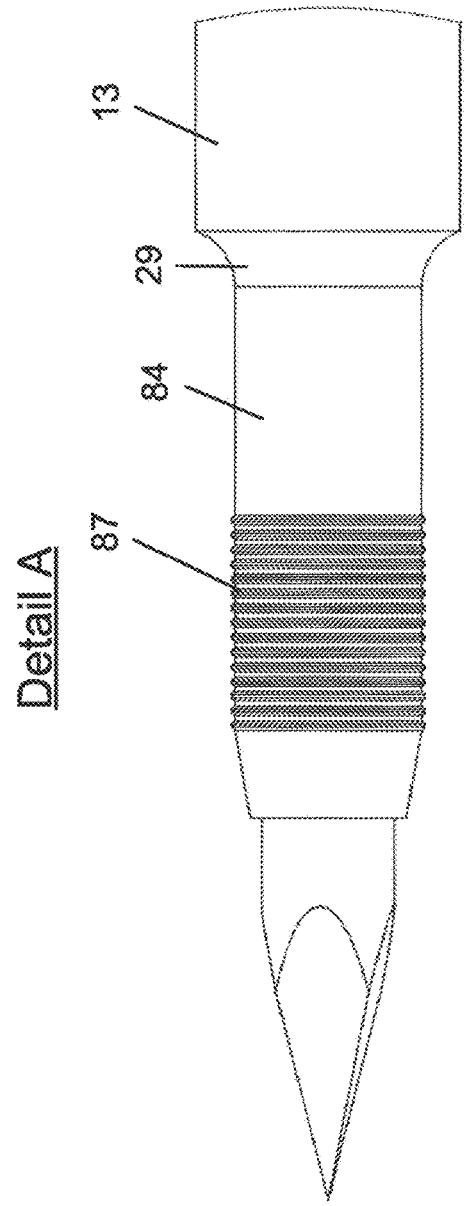
Fig. 8
Fig. 9
Detail A

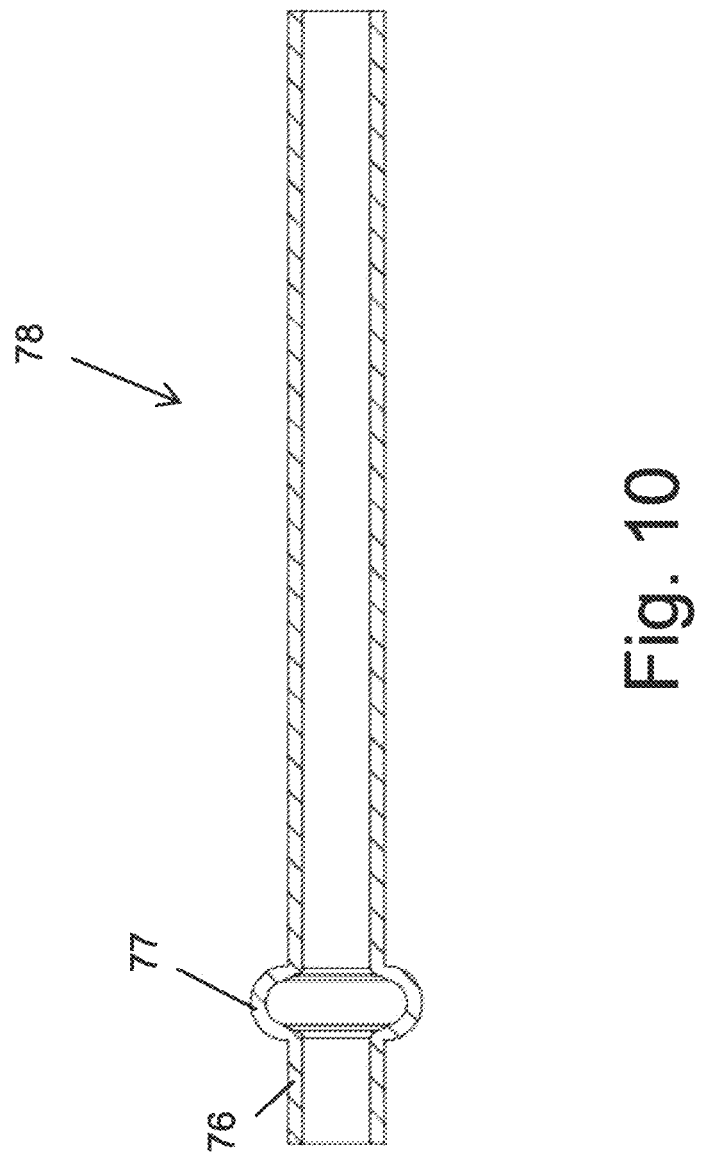

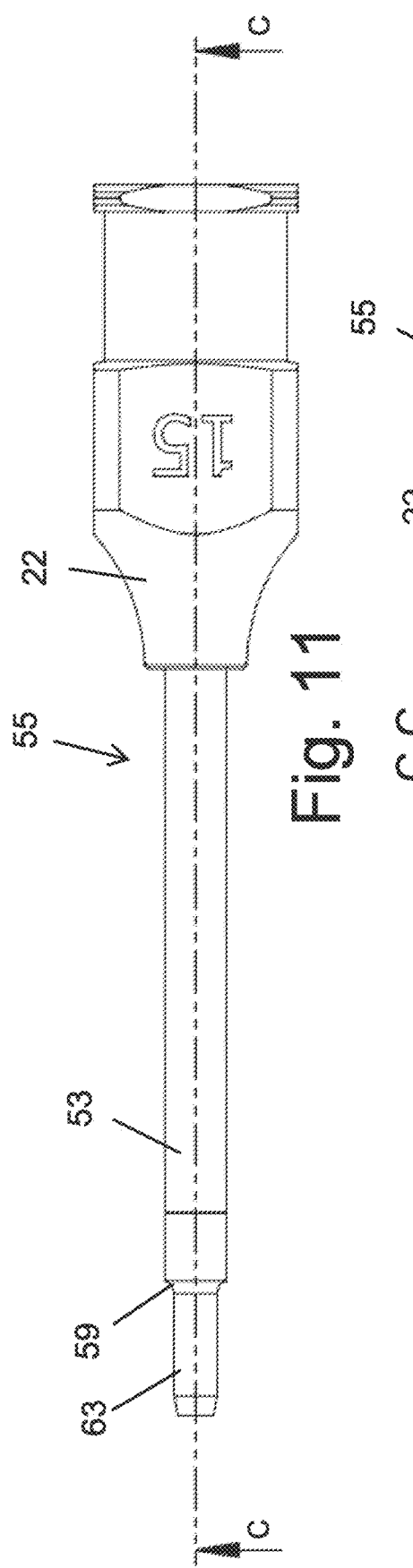
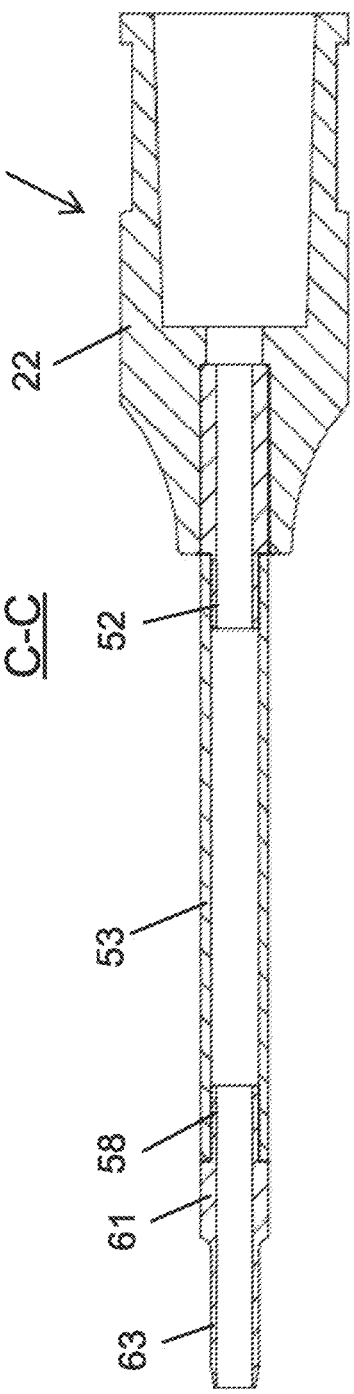

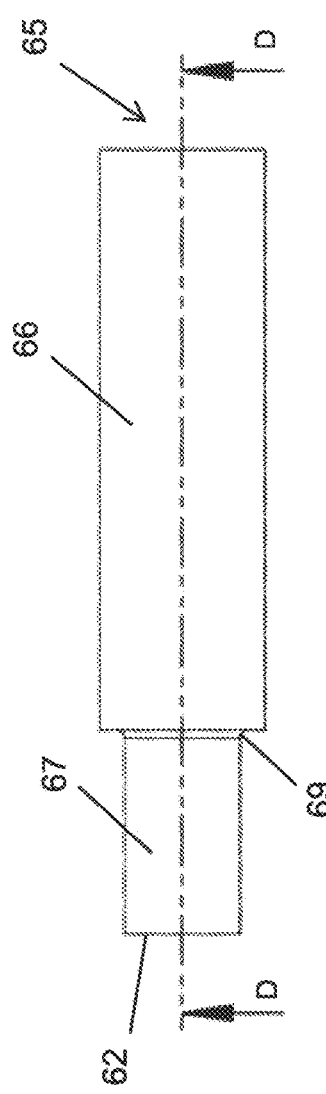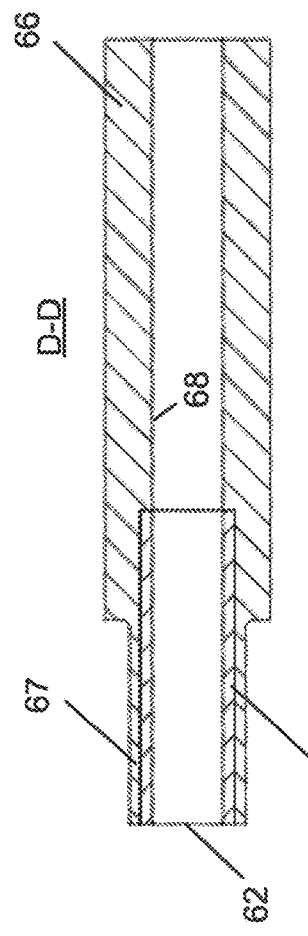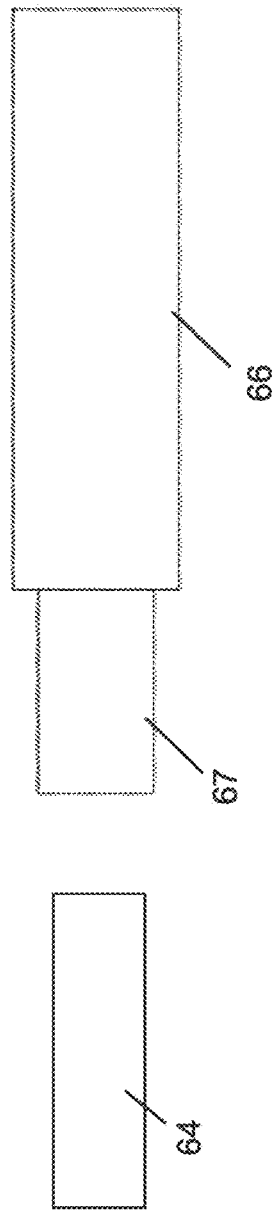

E-E

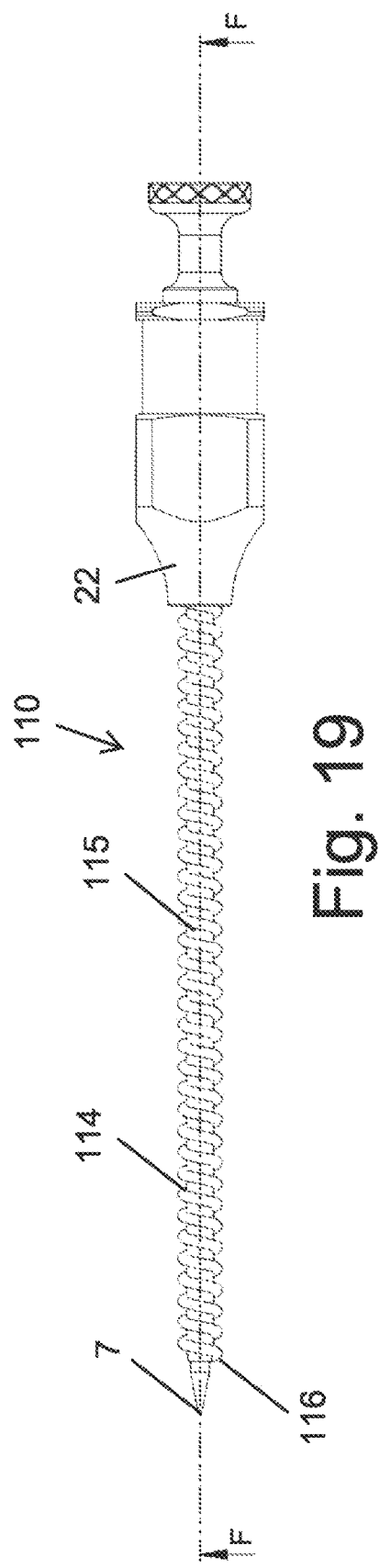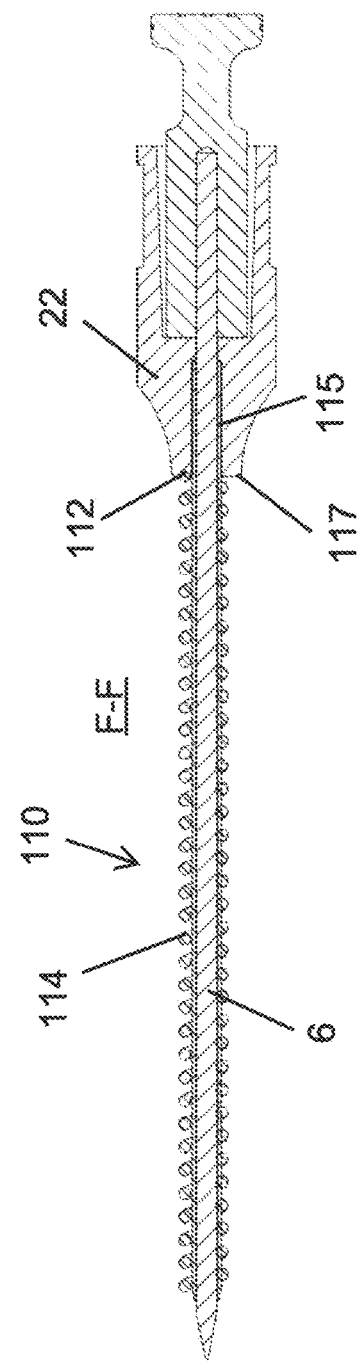
Fig. 19
Fig. 20

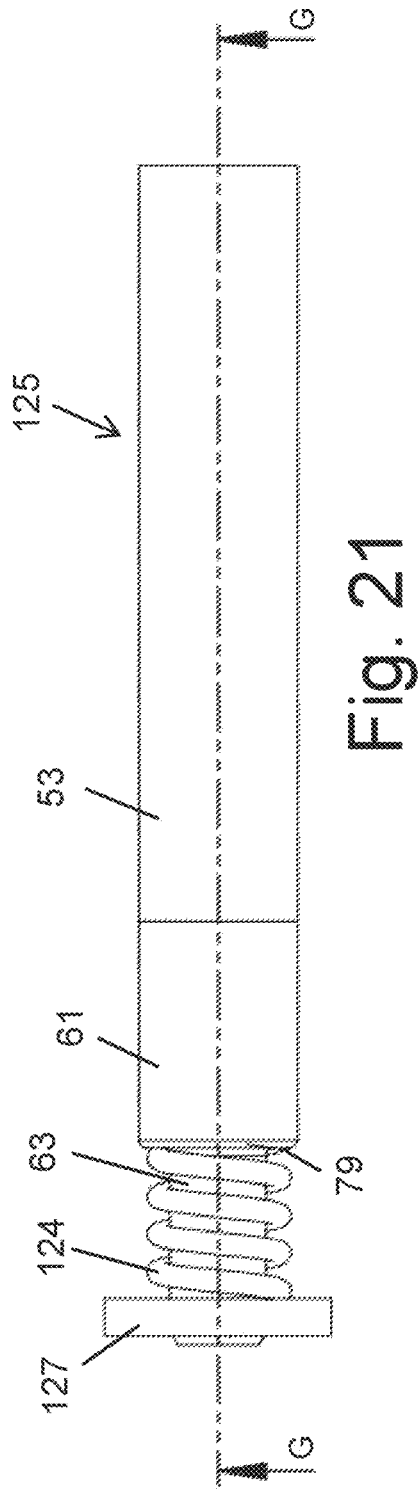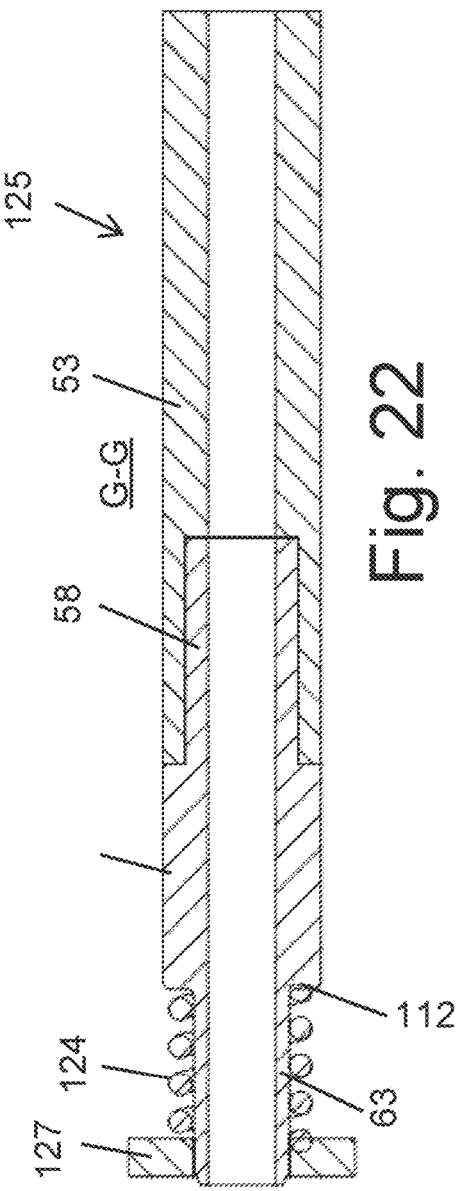

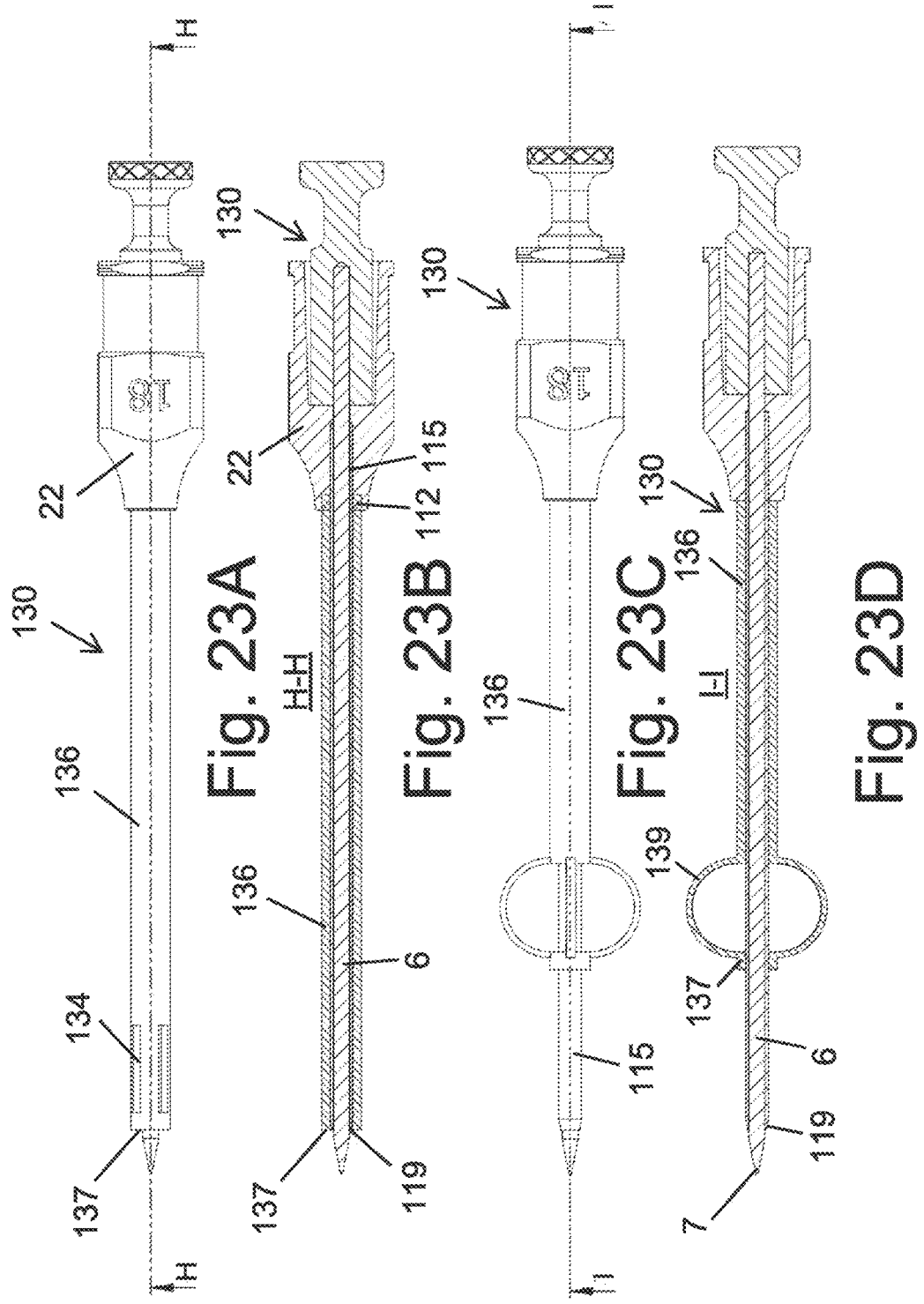

M-M

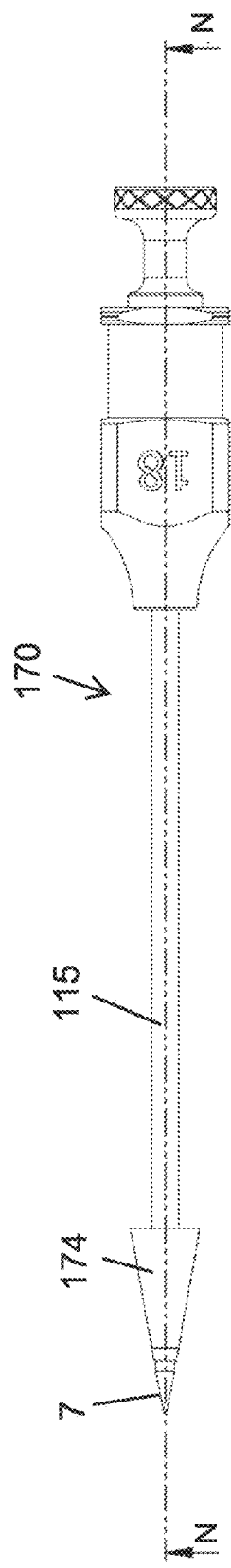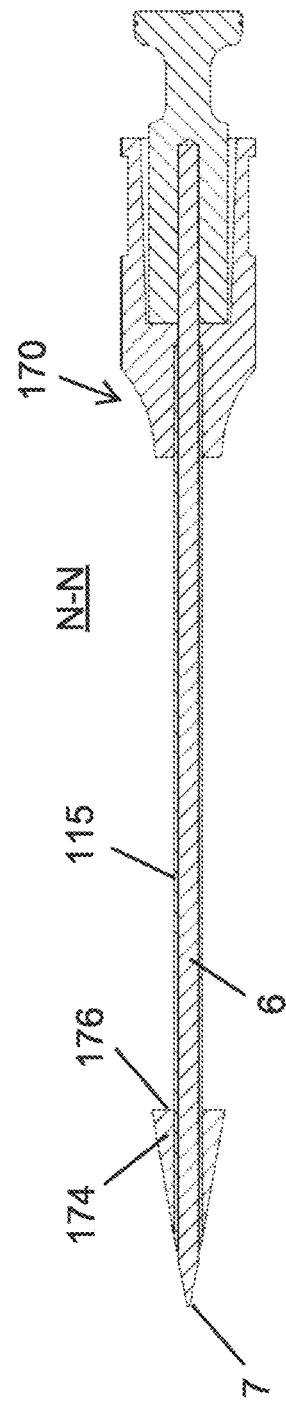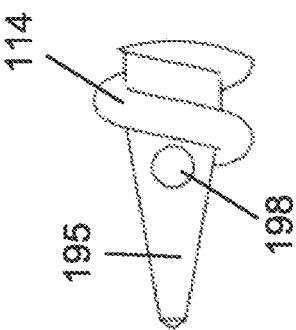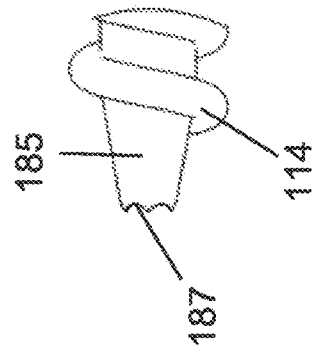

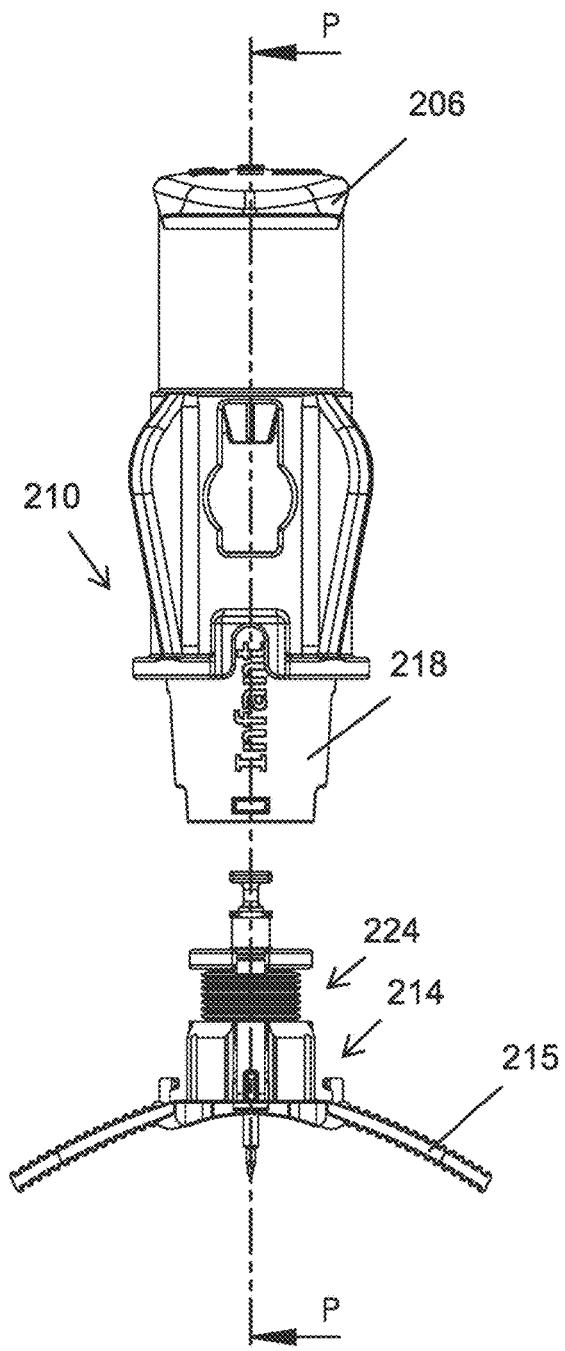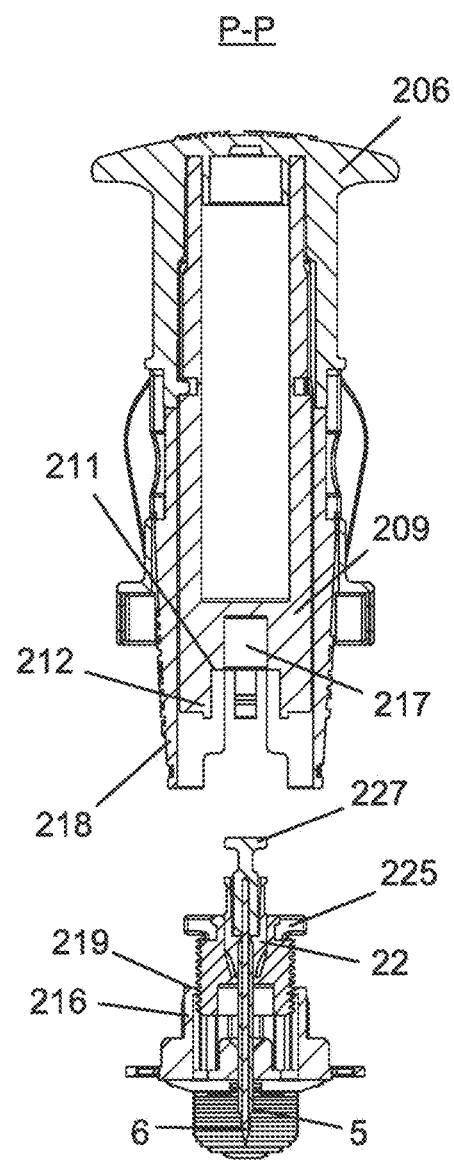
Fig. 31
Fig. 32

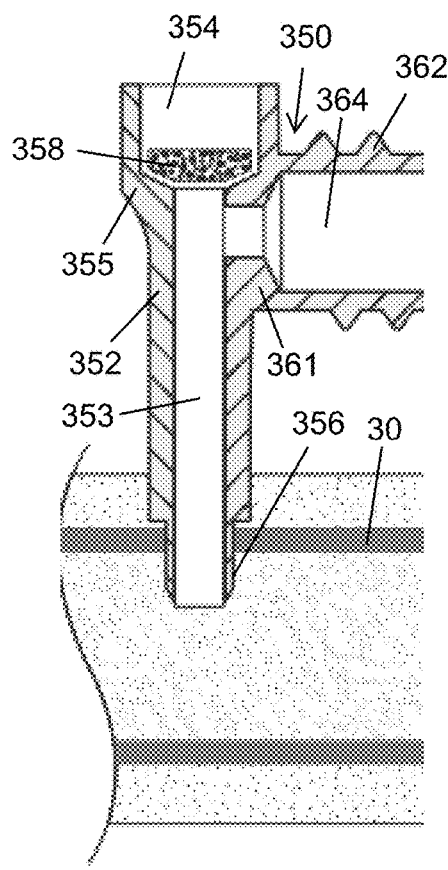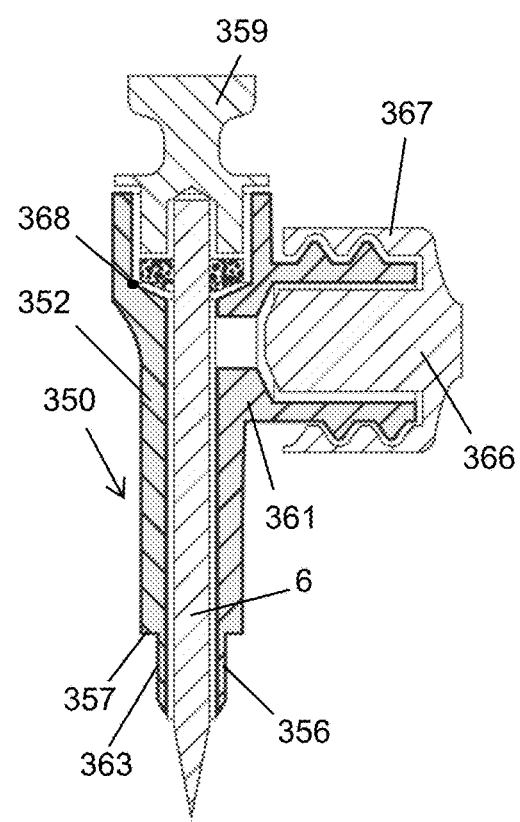
Fig. 38A     Fig. 38B
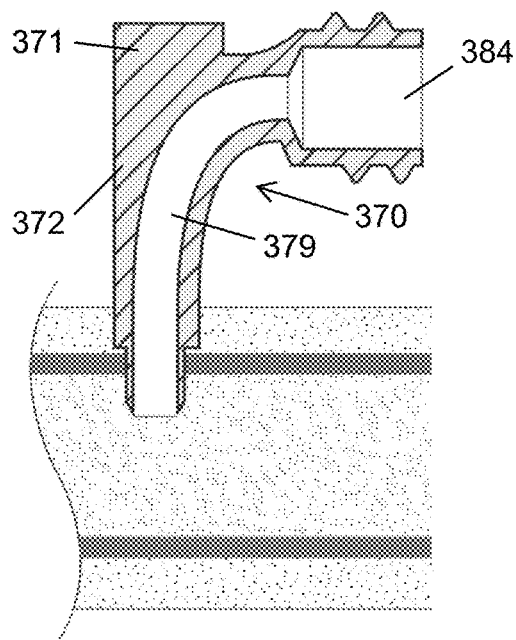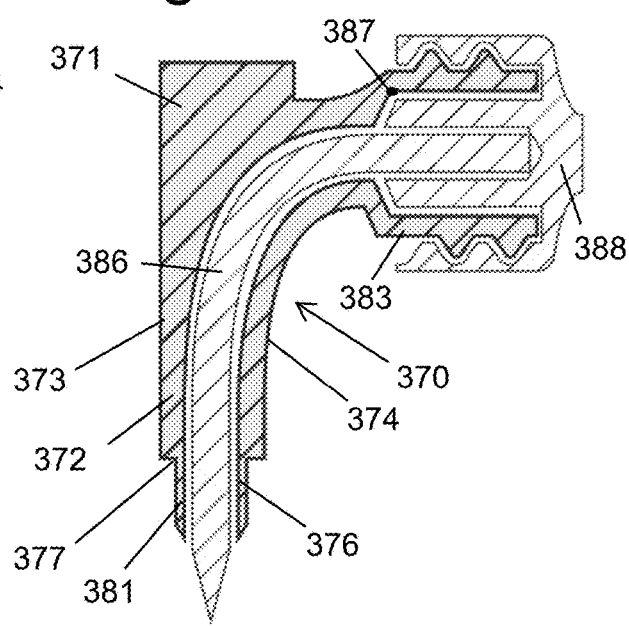
Fig. 38C     Fig. 38D

CANNULA FOR USE IN INTRAOSSEOUS INJECTIONS

This application is a Continuation-in-Part application of International Patent Application PCT/IL2017/051001 filed on Sep. 6, 2017, which claims priority from Israeli Patent Application No. 247684 filed on Sep. 7, 2016.

FIELD OF THE INVENTION

The present invention relates to the field of intraosseous devices for accessing bone marrow. More particularly, the invention relates to a cannula used in conjunction with an intraosseous device which facilitates penetration, generally to a desired depth through anatomical structures, of a needle in order to penetrate a bone cortex or access the bone marrow.

BACKGROUND OF THE INVENTION

The administration of medication to an injured or critically ill patient is many times delayed due to the difficulty in establishing an intravenous line. During such situations, a lifesaving alternative by which vascular access is quickly achieved is through intraosseous (IO) infusion, whereby fluids and medications are injected into a marrow cavity of a long bone such as the femur, tibia and humerus that drains into a central venous canal, and are then carried to the bloodstream.

The success of an IO infusion procedure is contingent upon penetration of the bone cortex to a patient-specific depth in order to access the bone marrow. The bone marrow will not be able to be accessed if tissue overlying a target bone is not sufficiently penetrated, for example when an incorrect needle length is employed or an excess amount of subcutaneous tissue exists, or alternatively if the needle is penetrated to an excessive depth, resulting in possible damage to healthy surrounding tissues and organs when the bone is overpenetrated after the needle has penetrated two opposite diametric regions of the bone.

Particularly, the bones of infants are very thin and are sometimes concealed by excessive overlying soft tissue. A health practitioner performing an IO penetration procedure therefore requires a high level of accuracy to locate the bone and to determine the proper depth of penetration for the IO needle.

Penetration of the sternum presents a high risk in overpenetration of its manubrium, which is joined to the clavicles and the cartilages of the first pair of ribs. A needle that unintentionally penetrates the distal cortex of the manubrium is liable to injure vital body parts such as the heart, lungs and the great vessels associated with the heart.

It would be desirable to provide a needle-receiving cannula with means for helping the health practitioner to determine when the bone marrow has been accessed, in accordance with a patient-specific penetration depth.

Many automatic IO devices, i.e. spring loaded or power driven, by which a needle is driven into the bone to a predetermined penetration depth, which, for some devices is user selected, are known from the prior art. An "automatic IO device" is one that does not require an active action to be taken by the user to stop the penetration of the needle. The needle is automatically driven to the predetermined penetration depth without intervention of the user and without knowledge as to which anatomical structures have been actually penetrated. At times, however, the penetration depth is incorrectly selected and the health practitioner is dismayed after determining that the bone marrow was not accessed following the penetration procedure.

Many terminable manual IO devices are also known from the prior art. A "terminable IO device", as referred to herein, is one that requires supervision of the needle penetration, in order to terminate the penetration procedure if it has been determined that a certain penetration depth has been achieved. During the course of a penetration procedure while the needle is being driven, whether manually or with the assistance of a power component which is able to be terminated for example by means of a trigger, the health practitioner is able to receive a tactile perception related to a change in resistance when the bone marrow is accessed, to indicate that further penetration by the device should be immediately terminated. Many times, however, the tactile perception is not noticeable when using a terminable IO device to penetrate thin bones or excessive tissue which overlies the target bone, or, on the other hand, when thick and dense bones are being penetrated and a relatively high level of force that diverts the attention of the health practitioner has to be applied.

There have been attempts in the prior art to provide a terminable IO device with means for controlling the depth of penetration.

Unimed SA, Lausanne, Switzerland discloses hemorrhoidal needles in its Medical Needles Catalog No. 2008-A, p 39 that have a proximal portion of a significantly greater diameter than a distal portion thereof.

U.S. Pat. No. 8,419,683 discloses an apparatus to access bone marrow at various target areas. The apparatus includes an intraosseous device operable to penetrate bone at a selected target area, a flange extending radially outward from the hub and configured to be supported by the skin surface to stabilize the intraosseous device, and a collar disposed on and engaged with exterior portions of a cannula and operable to control depth of penetration of the intraosseous device into bone and associated bone marrow.

In these prior art devices, the penetration depth controlling means is significantly spaced proximally from the distal tip of the needle, and the health practitioner needs to exert significant force during an IO penetration procedure to ensure sufficient penetration into the bone cortex. The needle is often speedily displaced as a result of the significant force application, and is consequently unintentionally caused to penetrate the distal cortex, or even to be overpenetrated. Penetration of the distal cortex leads to various complications, such as difficulty in releasing the needle after having penetrated the distal cortex, a low infusion flow rate due to the proximity of the distal end of the cannula to the distal cortex, and manifestation of the compartment syndrome during flow of fluids between the penetrated distal cortex and soft tissues.

It is an object of the present invention to provide a cannula of a terminable IO device with an indicator that helps to determine when the bone marrow has been accessed.

It is an additional object of the present invention to provide a cannula-mounted indicator that minimizes injury to the body during an intraosseous injection.

Other objects and advantages of the invention will become apparent as the description proceeds.

SUMMARY OF THE INVENTION

In one embodiment, a cannula for use in a terminable intraosseous device to indicate penetration of a cortex of a target bone comprises a cannula body; a penetrator-independent proximal bone penetration indicator (PBPI) associated with said cannula body for positively indicating initial penetration into said proximal bone, said PBPI comprising a roughened surface provided at a distal end of an outer surface of said cannula body without abruptly increasing an outer diameter of said cannula body, to assist in increasing an amplitude of vibrations that are generated immediately upon contact with a bone cortex of said proximal bone during performance of an intraosseous injection; and a stopper engageable with the bone cortex of said proximal bone, for preventing additional penetration, in addition to a given penetration depth to which said cannula body has been penetrated, into said proximal bone, wherein said roughened surface and said stopper constitute two distinct types of direct penetrator-independent tactile feedback during performance of the intraosseous injection into the proximal bone.

In one aspect, the stopper comprises one or more mechanical vibration intensifiers associated with the cannula body, in addition to the roughened surface, for increasing an amplitude of vibrations that are generated upon contact with the bone cortex during performance of the intraosseous injection.

In one aspect, the cannula body is a tubular body which comprises a main body and a secondary body distal to said main body, said main body being of a larger outer diameter than said secondary body, and the stopper is a step interface interfacing between said main and secondary bodies, positioned proximally to the roughened surface and defining a second vibration intensifier, wherein said secondary body is configured with the roughened surface to define a first vibration intensifier for generating vibration intensification immediately upon contacting the bone cortex.

In one aspect, the cannula body defines a lumen within which a stylet is insertable and for securely engaging a shaft of said stylet, when inserted within said lumen, wherein said lumen extends continuously and at a uniform bore diameter between the main and secondary tubular bodies.

In one aspect, the cannula is integrally formed with the main and secondary tubular bodies.

In one aspect, the secondary tubular body is attachable to the main tubular body.

In one aspect, the secondary tubular body is releasably attachable to the main tubular body.

In one aspect, the main tubular body is attachable to the secondary tubular body.

In one aspect, the radial protrusion of the step interface relative to an outer diameter of the secondary body is at least 0.1 mm.

In one aspect, the radial protrusion of the step interface relative to an outer diameter of the secondary body ranges from 0.1 to 3.0 mm.

In one aspect, the step interface is spaced from a tip of the stylet, when inserted within the lumen of the cannula, by a dimension that is no greater than 95% of a diameter of the marrow cavity of a target bone.

In one aspect, the step interface is spaced from the stylet tip by a dimension ranging from 1 mm to 30 mm.

In one aspect, the step interface is flexible.

In one aspect, the cannula is configured with a plurality of the step interfaces each of which constituting a mechanical vibration intensifier.

In one aspect, the main body radially protrudes from a first secondary body to define a first step interface, and said first secondary body radially protrudes from a second secondary body to define a second step interface.

In one aspect, the roughened surface is constituted by a plurality of irregularities that radially protrude from a smooth surface of the cannula body by a dimension of at least 20 microns, or by a plurality of longitudinally spaced rings that radially protrude from a smooth surface of the secondary body by a dimension of at least 20 microns.

In one aspect, the cannula further comprises an additional PBPI configured as a resilient element fixed at one end which becomes plastically deformed in response to increased resistance provided by the proximal bone to indicate initial penetration thereinto.

In one aspect, the resilient element is an atraumatic helical compression spring made of, or coated with, biocompatible material and which is fit about the cannula body and provides an indication as to depth of penetration as a function of spring resistance.

In one aspect, the cannula further comprises an additional PBPI configured as a frictionally engageable element by which a tactile indication of frictional engagement between said element and the cannula body and therefore of penetration into the proximal bone is transmittable to a health practitioner.

In one aspect, a distal end of the cannula body is configured with means for penetrating a bone cortex.

In one aspect, a longitudinal length of the roughened surface is at least a third of the longitudinal length of the secondary body.

In one aspect, the stopper is configured as a plurality of circumferentially spaced, radially expandable leaves, such that each leaf is defined by a longitudinal slit formed in the cannula body and is sufficiently long to undergo radial expansion when caused to contact the proximal bone cortex during the intraosseous injection.

In one aspect, the cannula body is a tubular body which comprises a main body and a secondary body distal to said main body, said main body being of a larger outer diameter than said secondary body, and wherein the stopper is configured with a plurality of circumferentially spaced integral scalpel blades protruding radially outwardly from said secondary body, each of said scalpel blades terminating with a sharpened and widened distal surface configured to contact the proximal bone cortex during the intraosseous injection. Each of the integral scalpel blades may be made of metallic or plastic material.

In one embodiment, a terminable intraosseous device comprises a penetrator for penetrating a bone cortex of a proximal bone; a cannula with a lumen comprising a main body and a thin-walled secondary body distal to said main body and proximal to said penetrator, wherein said main body is of a larger outer diameter than said secondary body to define a step interface interfacing between said main and secondary bodies that constitutes a mechanical vibration intensifier for increasing an amplitude of vibrations that are generated upon engaging the bone cortex following penetration of a predetermined depth thereinto; and a reinforcing member insertable within said lumen for reinforcing said secondary member and connected to a component of said cannula, wherein an infusion fluid is flowable through said lumen to a bone marrow cavity without being occluded by said reinforcing member and said penetrator.

In one aspect, the penetrator is a needle element that is integrally formed with the secondary body and the reinforcing member is a truncated solid-core post inserted within the lumen of the secondary body.

In one aspect, the reinforcing member is an insert positioned within, and fixedly attached to a wall of, the lumen of the secondary body and the penetrator is a solid needle element which is integrally formed with said insert, and wherein one or more apertures are formed in both the secondary body and said insert to facilitate discharge of the infusion fluid into the bone marrow cavity.

In one embodiment, a terminable intraosseous device adapted to indicate penetration into a cortex of a target bone, comprises a penetrator for penetrating a bone cortex of a proximal bone; a cannula body; a resilient element connected to said cannula body and configured to become plastically deformed and to cause a distance between said cannula body and said penetrator to become reduced in response to increased resistance provided by the proximal bone during initial penetration thereinto; and a penetrator-independent proximal bone penetration indicator (PBPI) associated with said cannula body for positively indicating initial penetration into said proximal bone, said PBPI comprising a visually indicative element which is concealed when the distance between said cannula body and said penetrator is a first distance and which is exposed when the distance between said cannula body and said penetrator is a second distance that is changed relative to the first distance.

BRIEF DESCRIPTION OF THE DRAWINGS

In the drawings:

FIG. 8 is a side view of a terminable IO device including a cannula according to another embodiment of the invention;

FIG. 9 is an enlargement of Detail A of FIG. 8;

FIG. 10 is a longitudinal cross sectional view of a cannula according to another embodiment of the invention;

FIG. 11 is a side view of a cannula according to another embodiment of the invention;

FIG. 12 is a cross sectional view of the cannula of FIG. 11, cut along plane C-C;

FIG. 13 is a side view of a cannula according to another embodiment of the invention;

FIG. 14 is a cross sectional view of the cannula of FIG. 13, cut along plane D-D;

FIG. 15 is a side exploded view of the cannula of FIG. 13;

FIG. 19 is a side view of an IO device according to another embodiment of the invention;

FIG. 20 is a cross sectional view of the IO device of FIG. 19, cut along plane F-F;

FIG. 21 is a side view of a cannula according to another embodiment of the invention;

FIG. 22 is a cross sectional view of the cannula of FIG. 21, cut along plane G-G;

FIG. 23A is a side view of an IO device according to another embodiment of the invention, shown in an unloaded position;

FIG. 23B is a cross sectional view of the IO device of FIG. 23A, cut along plane H-H;

FIG. 23C is a side view of the IO device of FIG. 23A, shown in a loaded position;

FIG. 23D is a cross sectional view of the IO device of FIG. 23C, cut along plane I-I;

FIG. 26A is a side view of an IO device according to another embodiment of the invention;

FIG. 26B is a cross sectional view of the IO device of FIG. 26A, cut along plane N-N;

FIG. 27 is an enlarged side view of the distal open end of a cannula according to one embodiment of the invention;

FIG. 28 is an enlarged side view of the distal open end of a cannula according to another embodiment of the invention;

FIG. 31 is a side view of the IO device of FIG. 29, showing the cannula in a post-penetration position and the needle housing and stabilizer separated from other components of the device;

FIG. 32 is a cross sectional view of the IO device of FIG. 31, cut along plane P-P;

FIG. 38A is a longitudinal cross sectional view of an embodiment of a side-tubulation cannula, shown when penetrated into a bone cortex and when a stylet and closures have been removed;

FIG. 38B is a longitudinal cross sectional view of the cannula of FIG. 38A, shown together with the stylet and closures and prior to a penetration procedure;

FIG. 38C is a longitudinal cross sectional view of another embodiment of a side-tubulation cannula, shown when penetrated into a bone cortex and when a stylet and closure have been removed;

FIG. 38D is a longitudinal cross sectional view of the cannula of FIG. 38C, shown together with the stylet and closure and prior to a penetration procedure;

DETAILED DESCRIPTION OF THE INVENTION

Figure 1:
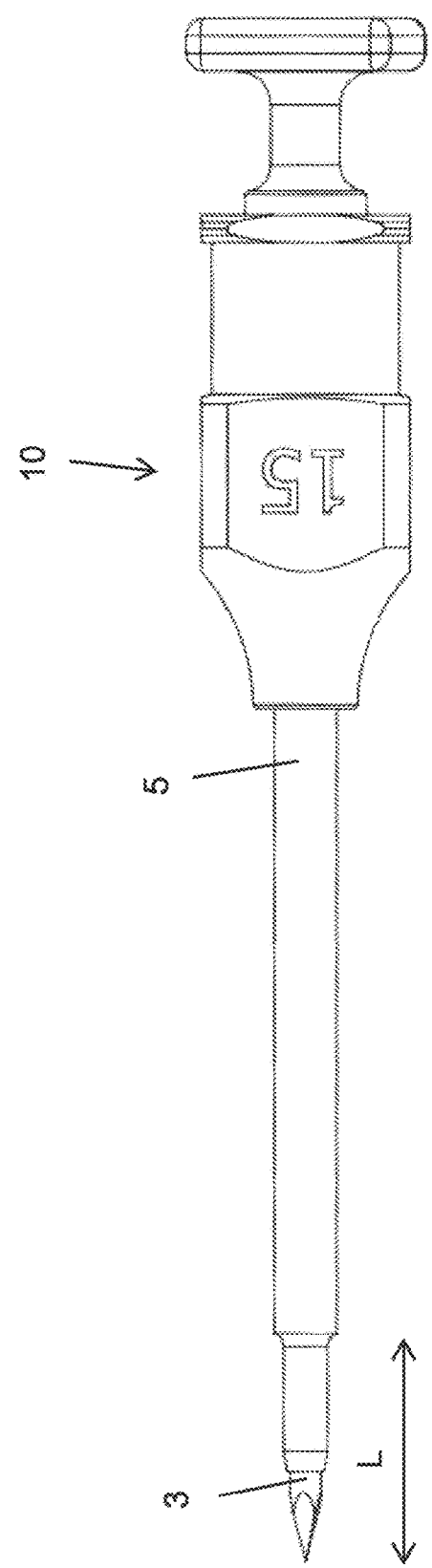
FIG. 1 is a side view of a terminable IO device, according to one embodiment of the present invention.

The cannula of the present invention is configured with a penetrator-independent proximal bone penetration indicator (hereinafter "PBPI"). The proximal bone is the circumferential bone region that is closest to the health practitioner during the performance of an IO penetration procedure, and is proximal to a distal bone region that would be penetrated if the proximal bone were overpenetrated, after the health practitioner failed to notice the tactile perception related to a change in resistance when the bone marrow was accessed.

A "penetrator" is the means by which a bone cortex is penetrated, usually a pointed tip or a serrated edge, and is generally provided at the extreme distal end of a stylet (being synonymous with a "trocar"), which is receivable within the cannula during an IO penetration procedure and is subsequently removable therefrom in order to infuse fluids into the marrow cavity, although the penetrator may be provided at the extreme distal end of the cannula without need of a stylet.

The cannula generally constitutes a terminable IO device, although the IO device may also comprise one or more additional components.

While the following description relates to a manual applied penetration procedure, it will be appreciated that the invention can be carried out with a powered terminable IO device such that the various elements are modified mutatis mutandis.

A health practitioner performing an IO penetration procedure, if properly attentive, will receive a tactile perception during initial penetration of the penetrator into the target bone. At times, however, the tactile perception is not noticeable, when penetrating excessive tissue which overlies the target bone, for example, and the target bone is at risk of overpenetration. As the PBPI is independent of the penetrator, the positive indication provided by the PBPI of bone penetration is more pronounced than the normal tactile perception received by a prior art IO penetration procedure and will help promote a more accurate IO penetration procedure.

In one embodiment, the PBPI comprises one or more mechanical vibration intensifiers for amplifying the tactile feedback that is available to a health practitioner during performance of an intraosseous injection with a terminable IO device. While the only tactile feedback that is available with the use of prior art devices is related to a change in resistance to the driving force of the stylet, normally provided by the hard and dense bone cortex but which is reduced when the stylet penetrates the bone marrow cavity, the vibration intensifier increases the amplitude of vibrations that are generated when the cortex of the proximal bone is immediately contacted during an IO penetration procedure, and these vibrations are transmitted to the hand of the health practitioner holding the proximal end of the stylet.

As an added safety precaution, one of the mechanical vibration intensifiers may also function as a stopper engageable with the bone cortex for preventing additional penetration of the stylet or of any other penetrator. The cannula is thus configured with two noticeable types of direct penetrator-independent tactile feedback during performance of an intraosseous injection into the proximal bone. The first type generates vibration intensification immediately upon penetrating the bone cortex to indicate to the health practitioner that the proximal bone has been penetrated and that care must be taken to avoid penetration of the distal cortex. The second type of tactile feedback provided to the health practitioner is in the form of resistance induced by a stopper, which may be positioned proximally to the PBPI. When the stopper engages the bone cortex of the proximal bone, the cannula is prevented from additionally penetrating the bone cortex, when the magnitude of force applied by the health practitioner is not significantly increased. This second type of tactile feedback alerts the health practitioner that the cannula has penetrated the bone cortex to a suggested depth and that the penetration procedure should be soon terminated to prevent overpenetration.

In other embodiments, the PBPI provides visual or audible feedback during performance of an intraosseous injection into the proximal bone. The cannula may be additionally configured with a stopper to prevent additional penetration into the bone cortex.

FIGS. 1-18 illustrate a first embodiment of the invention wherein the PBPI comprises a plurality of vibration intensifiers and the cannula is configured with a step interface constituting one of the vibration intensifiers.

In the implementations illustrated in FIGS. 1-10, the cannula is made of a single component.

FIGS. 1-4 illustrate the components of an IO device 10 for performing an intraosseous injection.

Figure 2:
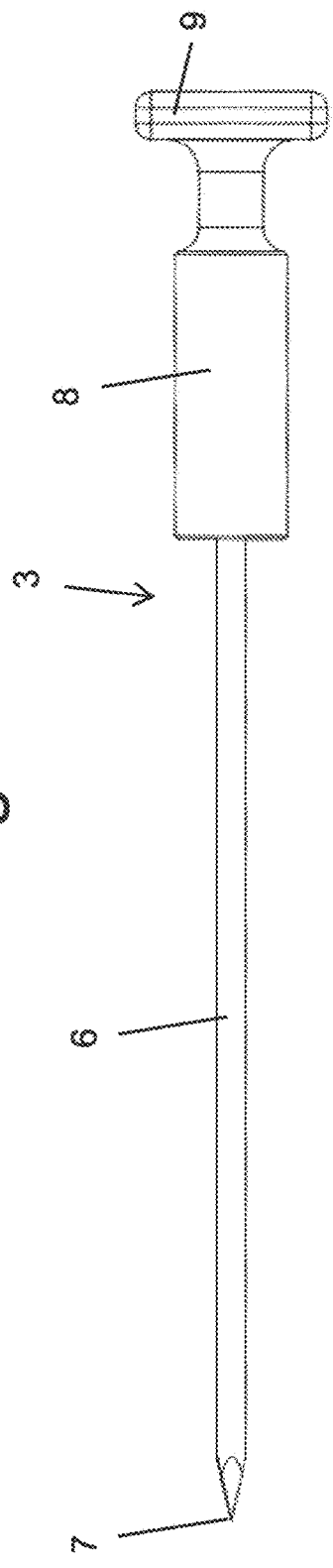
FIG. 2 is a side view of a stylet used in conjunction with the terminable IO device of FIG. 1.

IO device 10 shown in FIG. 1 comprises stylet 3 and cannula 5. As shown in FIG. 2, stylet 3 has an elongated stylet shaft 6 usually made from metal such as stainless steel, e.g. SAE 302 or 304, in order to prevent bending during penetration, a distal pointed tip 7 for piercing both skin tissue and bone tissue, a hub 8, e.g. rectilinear and made from plastic or metal such as brass 360, connected to the proximal end of stylet shaft 6, and a handle 9 connected to the proximal end of hub 8. Tip 7 may be of the pencil point type or may be phased.

Figure 3:
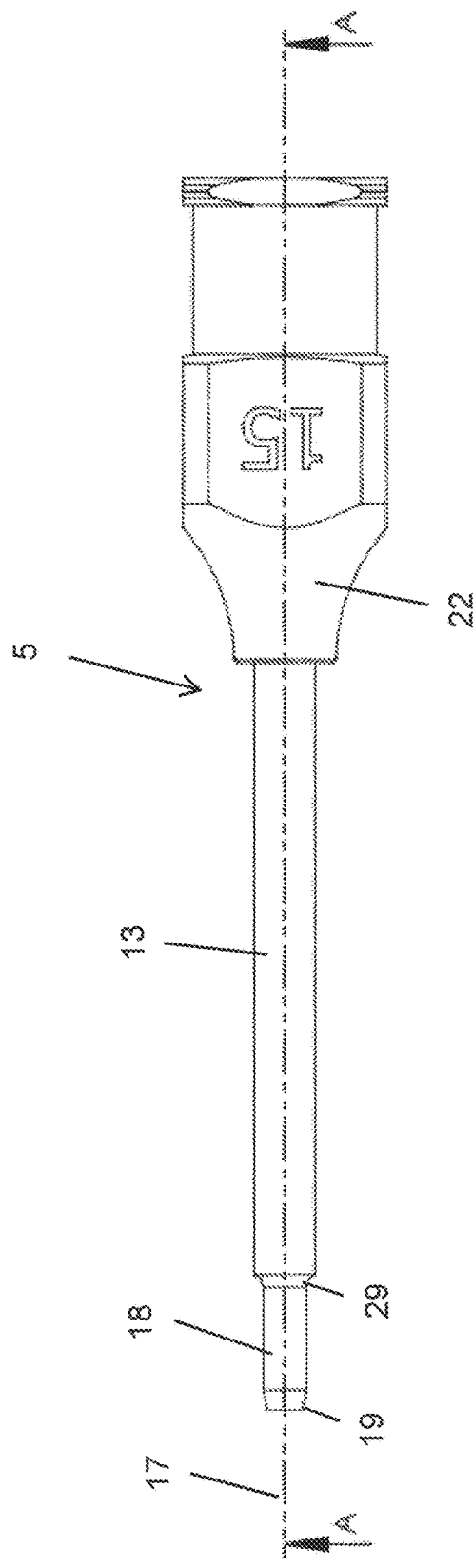
FIG. 3 is a side view of a cannula used in conjunction with the terminable IO device of FIG. 1.
Figure 4:
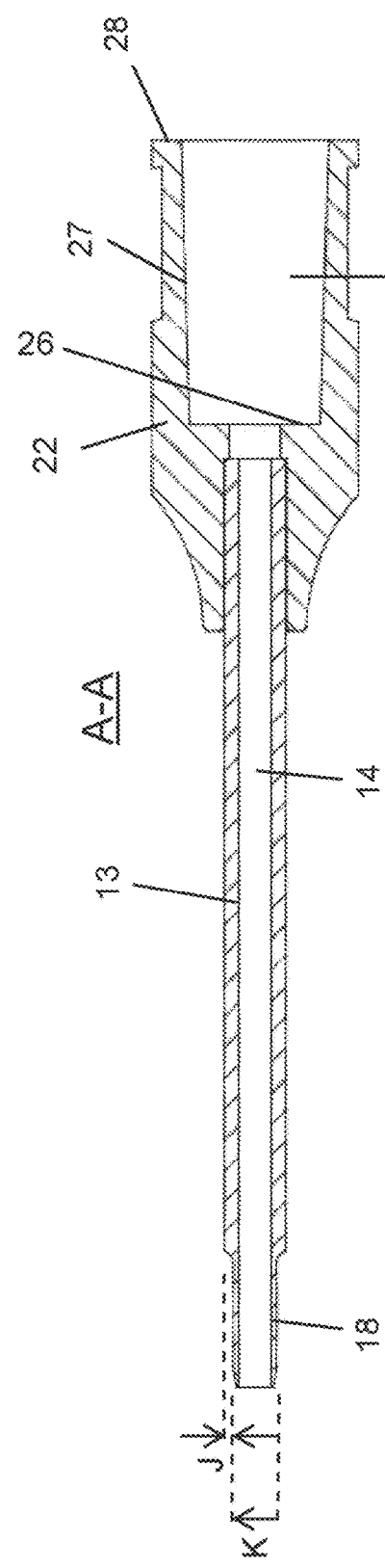
FIG. 4 is a cross sectional view of the cannula of FIG. 3, cut along plane A-A.

As shown in FIGS. 3 and 4, cannula 5 has an elongated main annular body 13 delimiting the central bore 14 into which the stylet shaft is insertable with a tight fit and defining the longitudinal axis 17 of the cannula. Main body 13 may be manufactured from flexible plastic or metal such as SAE 316 since it is strengthened by the stylet shaft inserted therewithin. Extending distally from main body 13, and integrally formed therewith, is a secondary tubular body 18 of a significantly shorter length than main body 13 and which also delimits central bore 14 such that the inner surface of central bore 14 is continuous throughout bodies 13 and 18. Secondary body 18 terminates with a tapered end 19 that facilitates a secured engagement with the stylet when inserted within cannula 5.

Cannula 5 may be machined, such as by a CNC-controlled lathe, from e.g. a 18 G/8 G thick-walled tube defining main body 13 to form thin-walled secondary body 18 having dimensions of 18 G/17 G.

Cannula 5 may also be formed by deforming a thick-walled tube to produce secondary body 18, or alternatively by deforming a thin-walled tube to produce main body 13.

Cannula 5 also has a hub 22 that is connected to, or integrally formed with, a proximal region of main body 13. Hub 22, which may be manufactured from plastic or metal such as brass 360, is considerably thicker than main body 13, and is configured with an internal cavity 24 that coincides with the proximal hub edge 28 and is in communication with central bore 14. Since cannula 5 is adapted for insertion within the hard surface of the bone cortex, distal cavity wall 26 may be configured with an inner step having a smaller inner diameter than the outer diameter of main body 13, to prevent disengagement of the cannula main body from the cannula hub. Cavity 24 is formed symmetrically with respect to longitudinal axis 17, and may be complementary to stylet hub 8. Thus when stylet 3 is inserted into central bore 14 via cavity 24 with the assistance of handle 9 until stylet hub 8 is in abutting relation with the distal cavity wall 26, and possibly with the peripheral cavity walls 27, and stylet shaft 6 is in secured engagement with tapered end 19 of secondary tubular body 18, stylet shaft 6 is assured of being positioned coaxially in a fixed position with respect to main body 13 and secondary body 18. Cavity 24 is configured to permit connection with an additional infusion related component, such as an extension set or a syringe.

The diameter of main body 13 is greater than secondary body 18, and the step interface 29 between main body 13 and secondary body 18 constitutes a vibration intensifier that increases the amplitude of vibrations which are generated when the bone cortex is contacted thereby during an IO penetration procedure. In order to provide sufficient vibration intensifying capability, the radial protrusion J of interface 29 relative to diameter K of secondary body 18 is greater than 0.1 mm for an increased surface area that is able to contact the bone cortex, but less than 3.0 mm, for example less than 1.5 mm or less than 1 mm, in order to prevent formation of an excessively large bore in the skin or bone during the penetration procedure. This range of difference in diameter is based on both the minimal needle gauge differences for high density bones normally found in adult patients of 18 G/17 G and on the maximal needle gauge differences for low density bones normally found in infant patients of 18 G/8 G. This range of difference in diameter also facilitates penetration into various anatomical sites having different bone density. Diameter K of secondary body 18 is slightly greater than the diameter of stylet shaft 6 to ensure a secured engagement between tapered end 19 and stylet shaft 6. The diameter of central bore 14, and therefore of cannula 5, may be customized according to patient age, for example 18 G/14 G for pediatric patients and 15 G/13 G for adults.

When the difference in the diameter D of main body 13 and the diameter d of secondary body 18 is greater than a predetermined value, as indicated in Table I, step interface 29 is able to function as a stopper due to the relatively large force needed to overcome the bone resistance. However, when the difference in diameter is less than the predetermined value, a health practitioner is able to overcome the bone resistance despite the presence of step interface 29 and increase the depth of penetration into the bone by applying a low to medium force.

TABLE I

Penetrability of Step Interface

| Use | Required Force Intensity | Thin tube d | Thick tube D | Diameter difference D − d |
|---|---|---|---|---|
| Pediatric | Low | 18G (1.27 mm) | 15G (1.82 mm) | 0.55 mm |
| Adult | Low | 15G (1.82 mm) | 14G (2.1 mm) | 0.28 mm |
| Pediatric | Medium | 18G (1.27 mm) | 14G (2.1 mm) | 0.83 mm |
| Adult | Medium | 15G (1.82 mm) | 13G (2.4 mm) | 0.58 mm |
| Pediatric | High | 18G (1.27 mm) | 13G (2.4 mm) | 1.13 mm |
| Adult | High | 15G (1.82 mm) | 11G (3.04 mm) | 1.22 mm |
| Pediatric | Stopper | 18G (1.27 mm) | 12G (2.7 mm) | 1.43 mm |
| Adult | Stopper | 15G (1.82 mm) | 10G (3.4 mm) | 1.58 mm |

A low required force intensity corresponds to a low force of only 40-80 N that needs to be applied by the health practitioner to overcome the bone resistance and to cause penetration of step interface 29 into the bone cortex. A medium required force intensity corresponds to a medium force of 100-150 N, and a high required force intensity corresponds to a high force of only 170-200 N. When step interface 29 functions as a stopper, as a result of a difference in diameter of greater than a predetermined value, penetration of step interface 29 into the bone cortex is prevented even when the health practitioner applies a force of 250-300 N.

Step interface 29 is selected to be spaced from stylet tip 7 by a longitudinal dimension L that is equal to the sum of the length of secondary body 18 and the length of the stylet portion projecting from secondary body 18. Dimension L is no greater than the diameter of the target bone in order to alert the health practitioner after the bone cortex has been penetrated and prior to being overpenetrated, and is preferably less than 90% the diameter of the target bone, for example 50% the diameter of the target bone, ranging from 1 mm for infants or for small-cavity bones to 30 mm, e.g. 10 mm, for adults or for large-cavity bones. The selected longitudinal dimension L of course is dependent upon the desired penetration depth, anatomical site and age group. In addition, the minimal penetration depth has to be larger than the cortex thickness in order to ensure that the marrow cavity will be accessed.

Figure 5:
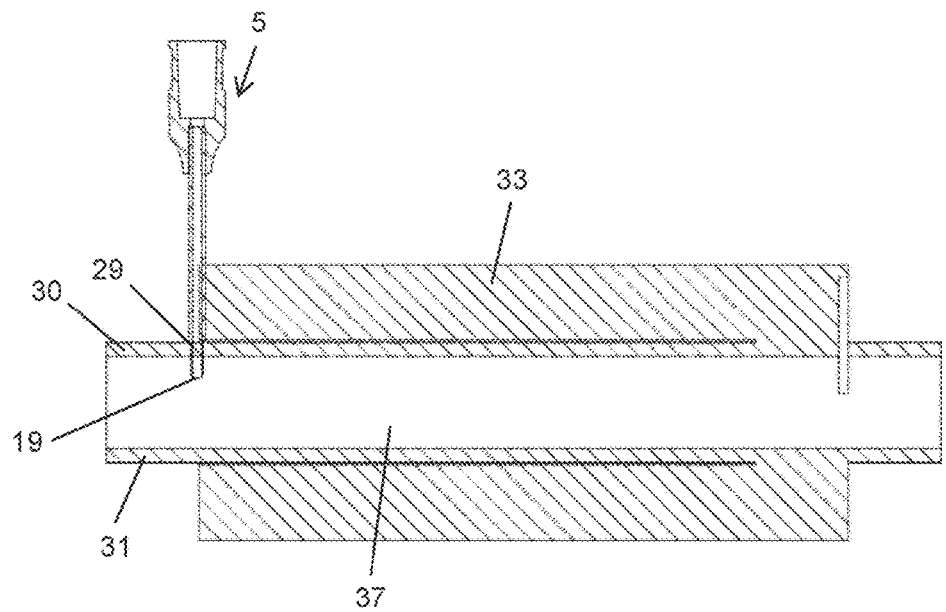
FIG. 5 is a medial cross sectional view of a bone bearing anatomical structure, showing the immobilization of the cannula of FIG. 3 within the corresponding bone cortex.

FIG. 5 is a cross sectional view of an anatomical structure at a bone penetration site, showing the immobilization of cannula 5 within proximal bone cortex 30 and the overlying soft tissue 33 while marrow cavity 37 is accessed by the cannula distal end 19, after the stylet has been removed from the cannula following an IO penetration procedure and in anticipation of an infusion procedure.

Further penetration of cannula 5 into distal bone cortex 31 is prevented by step interface 29 functioning as a stopper, while contacting the outer surface of proximal bone cortex 30. Although additional penetration into distal bone cortex 31 is normally prevented by step interface 29 when an average-magnitude force is applied during a penetration procedure, it should be understood that application of an increased-magnitude force by the health practitioner to cannula 5 is able to overcome the holding force of step interface 29 and the reactive force of proximal bone cortex 30 to cause an increase in the bore size of the bone penetration initiated by the step interface and to permit additional bone penetration. Since the attention of the health practitioner may be diverted during application of the increased-magnitude force, leading to safety risks such as overpenetration, step interface 29 advantageously also constitutes a mechanical vibration intensifier which transmits vibrations upon contacting proximal bone cortex 30, to signal to the health practitioner that the penetration procedure should be immediately terminated.

Figure 6:
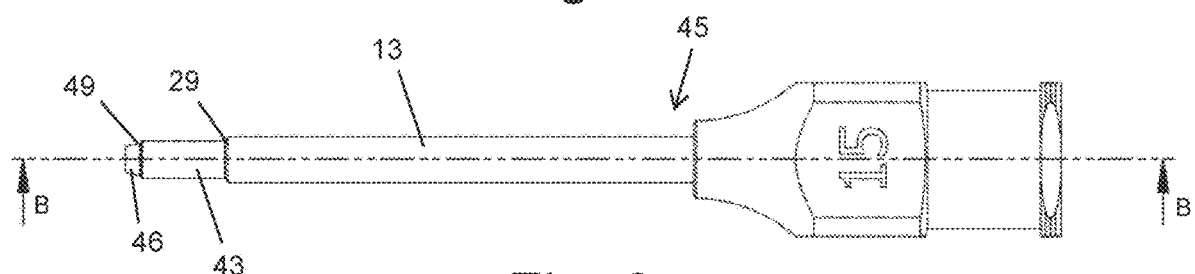
FIG. 6 is a side view of a cannula according to another embodiment of the invention.

FIG. 6 illustrates a cannula 45 which is configured with a plurality of step interfaces and with a corresponding number of integrally formed secondary bodies defining the step interfaces, to increase the sensory amplification. Each step interface may have the same radial protrusion from the secondary body, or alternatively may have a different radial protrusion. For example, cannula 45 is configured with two step interfaces, the first interface 29 as described hereinabove and the second interface 49 located distally to the first interface 29. Main body 13 radially protrudes from the first secondary body 43, e.g. by dimension J, and the first secondary body 43 radially protrudes from the second secondary body 46. Although the radial protrusion of second interface 49 relative to second secondary body 46 is generally less than the dimension needed to function as a stopper with respect to an applied average-magnitude force, second interface 49 nevertheless induces vibrations upon contacting the bone cortex, to indicate to the health practitioner that the penetration procedure should be soon terminated.

Figure 7:
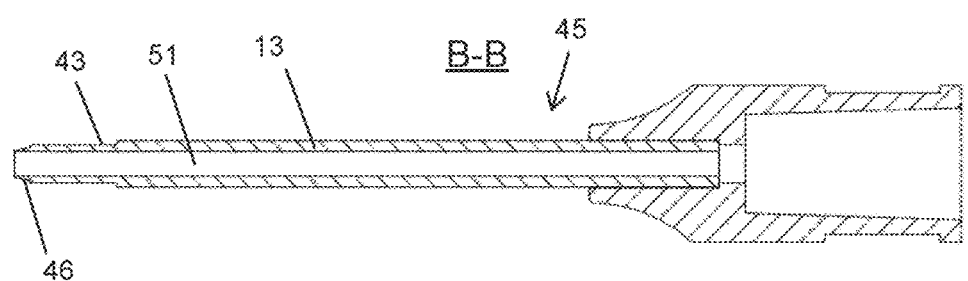
FIG. 7 is a cross sectional view of the cannula of FIG. 6, cut along plane B-B.

As shown in FIG. 7, the inner surface of central bore 51 formed in cannula 45 may be continuous throughout bodies 13, 43 and 46.

FIGS. 8 and 9 illustrate a terminable IO device 90 comprising cannula 85 which is configured with a secondary body 84 that is positioned distally to step interface 29 at main body 13 and that is surface roughened to provide vibration intensification. Secondary body 84 may be surface roughened by a plurality of longitudinally spaced rings 87 that radially protrude from the smooth surface of secondary body 84 by a dimension of at least 20 microns up to a radial protrusion of approximately 500 microns, to ensure that the outer diameter of secondary body 84 will not be abruptly increased. Thus the contact made with the bone cortex by the surface roughening, or by any other desired type of continuous or discontinuous irregularities, will become immediately noticeable to the health practitioner. The irregularities may be formed by reducing the diameter of the remaining portion of secondary body 84 between one irregularity and another or by applying material to the smooth surface of secondary body 84. Rings 87, for example, may be adhesively affixed to the smooth surface of secondary body 84. The longitudinal length of the roughening provided by rings 87 is generally at least a third of the longitudinal length of secondary body 84, to facilitate receiving the tactile feedback immediately upon initial penetration into the rigid and incompressible proximal bone as a result of its being more noticeable. Cannula 85 may be integrally formed with main body 13 and secondary body 84, or alternatively main body 13 and secondary body 84 may be connected together according to any embodiment described herein.

FIG. IO illustrates a cannula 78 that is deformed from a thin-walled tube, such as by applying a large-magnitude axial force simultaneously to its proximal and distal ends, to produce radial protrusion 77 that defines a step interface. Radial protrusion 77 may be curved as shown, or may be pointed. The portion 76 of the tube outer surface distal to radial protrusion 77 may be surface treated with irregularities as described above to provide vibration intensification immediately upon penetrating a bone cortex.

In FIGS. 11-18, the cannula is made of two or more different components which are connected to each other.

Reference is first made to cannula 55 of FIGS. 11 and 12. While hub 22 is made of a rigid material such as a metallic material, the main tubular body 53 may be made of a flexible material such as rubber that is secured to an internal annular post 52 which distally extends from hub 22. The flexible main body 53 may be formed integrally with the secondary body to define step interface 59. Alternatively, tubular secondary body 63 together with a proximal portion 61 thereof having a larger diameter which is essentially equal to the diameter of main body 53 to define step interface 59 is secured to main body 53 by means of an annular post 58 extending proximally from proximal portion 61. Post 58 is adapted for insertion within, and connection to, main body 53 by connection means including adhesion, laser welding, press fitting and threaded engagement. When main body 53 has a relatively thick wall, its inner diameter may be reduced by a material removal tool such as a drill and then connected to post 58. Secondary body 63, which may be made of a rigid material such as a metallic material, may be detachable from main body 53, and main body 53 may be detachable from hub 22.

Secondary body 63 may be surface treated with irregularities to provide vibration intensification immediately upon penetrating a bone cortex. Thus the health practitioner is provided with feedback as to whether the marrow cavity has been accessed. If the marrow cavity has not been accessed, the penetration procedure is continued until the health practitioner is provided with feedback by step interface 59 to indicate whether the marrow cavity has been accessed.

Figures 41, 42, 43:
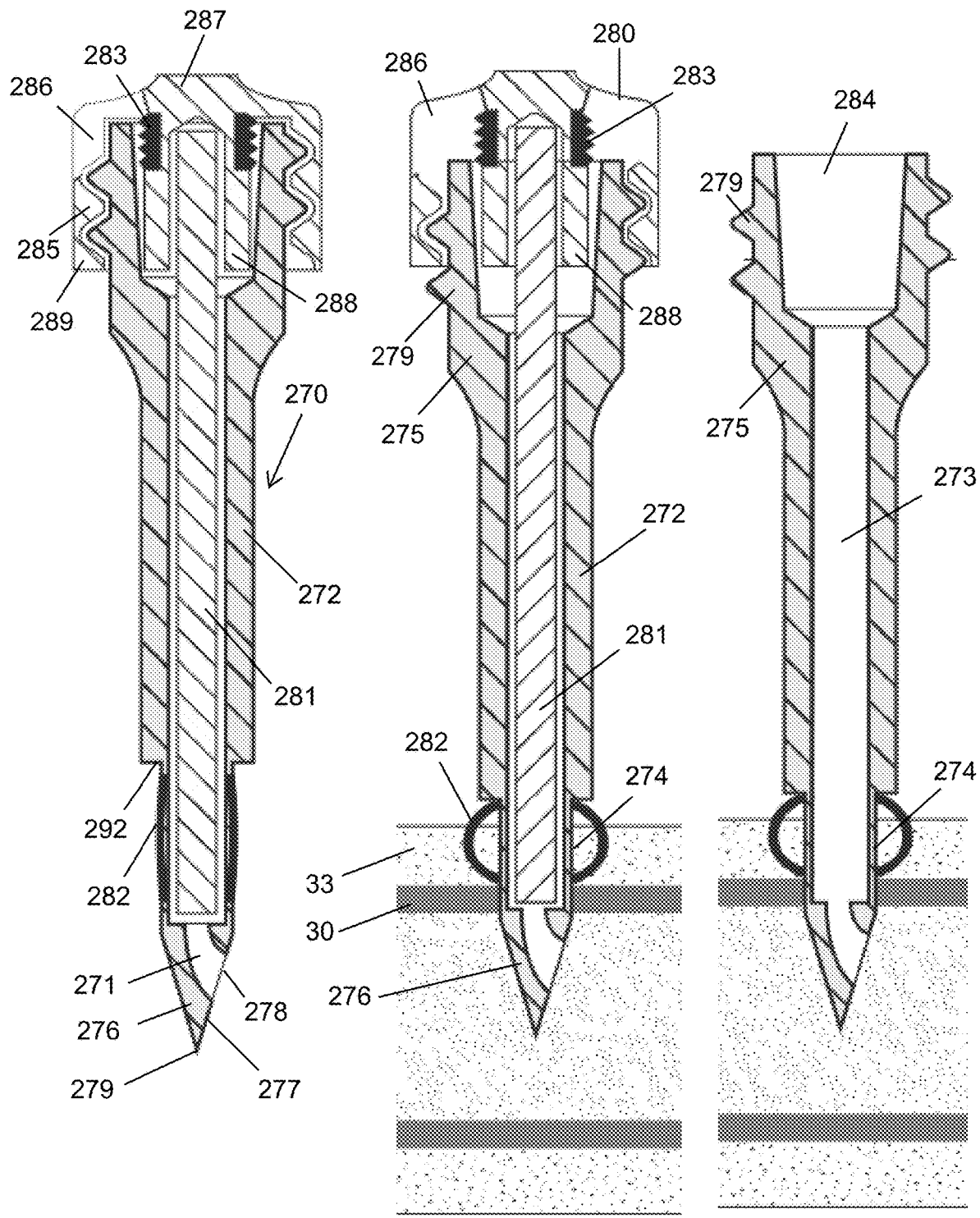
FIG. 41 is a longitudinal cross sectional view of an IO device according to another embodiment of the invention.
FIG. 42 is a longitudinal cross sectional view of the IO device of FIG. 41, shown following penetration of the bone cortex.
FIG. 43 is a longitudinal cross sectional view of the IO device of FIG. 41, shown when penetrated into a bone cortex and when a reinforcing post has been removed.
Figure 49:
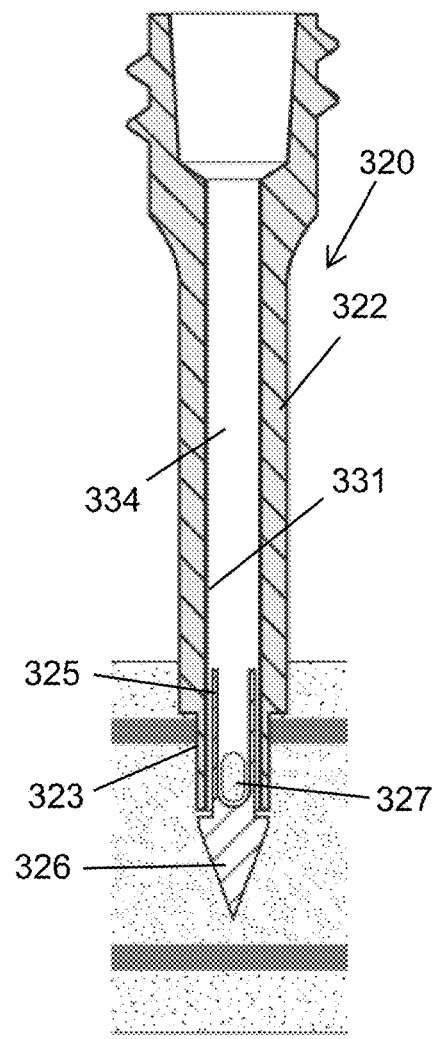
FIG. 49 is a longitudinal cross sectional view of the IO device of FIG. 48, shown following penetration of the bone cortex.

In FIGS. 13-15, annular main body 66 of cannula 65 is integrally formed with a distal thin-walled secondary body 67 of a smaller diameter to define a step interface 69 therebetween. As referred to herein, a "thin-walled secondary body" that needs to be reinforced has a wall thickness of less than 0.2 mm, for example up to 0.1 mm. Material is removed from the common inner surface 68 of main body 66 and secondary body 67 such as by a drill for a predetermined distance from the distal end 62 of cannula 65, e.g. 2-5 mm. A reinforcing tube 64 is then inserted within, and connected to, the resurfaced inner surface by connection means including adhesion, laser welding, press fitting and threaded engagement. Other reinforcing means may be employed, for example as illustrated in FIGS. 41 and 49. The outer surface of secondary body 67 may be surface treated with irregularities as described above.

Figure 16:
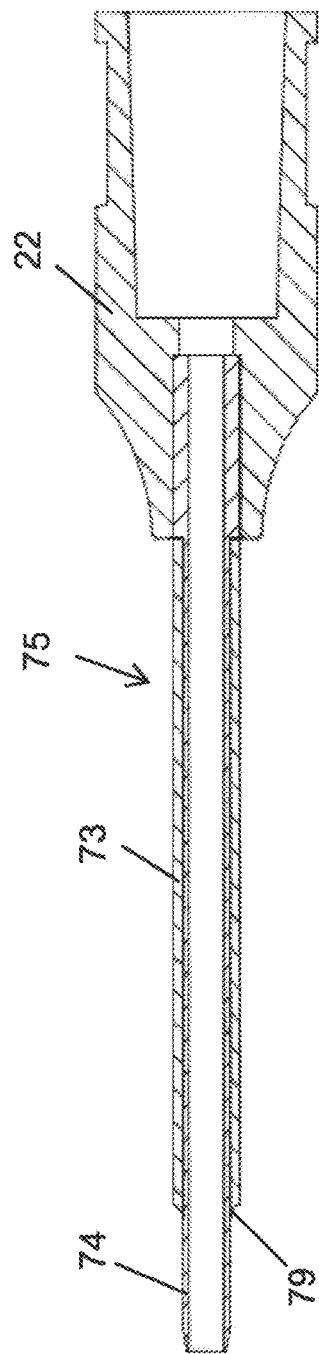
FIG. 16 is a longitudinal cross sectional view of a cannula according to another embodiment of the invention.

Alternatively, as shown in FIG. 16, the entire secondary body 74 of cannula 75, which may be configured as an annular post extending distally from hub 22, may be made from metallic material, while main body 73 may be made of flexible plastic or rubber material and adhesively connected to secondary body 74 to define step interface 79. The provision of a flexible step interface 79 minimizes injury in the vicinity of the penetration site, yet is able to function as both a mechanical vibration intensifier to transmit induces vibrations when the bone cortex is contacted and as a stopper to prevent additional penetration.

It will be appreciated that main body 73 may also be made of metallic material, and that the outer surface of secondary body 74 may be surface treated with irregularities as described above.

Figure 17:
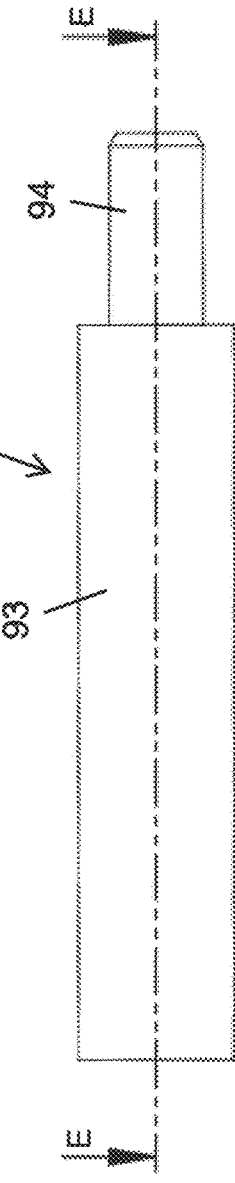
FIG. 17 is a side view of a cannula according to another embodiment of the invention.
Figure 18:
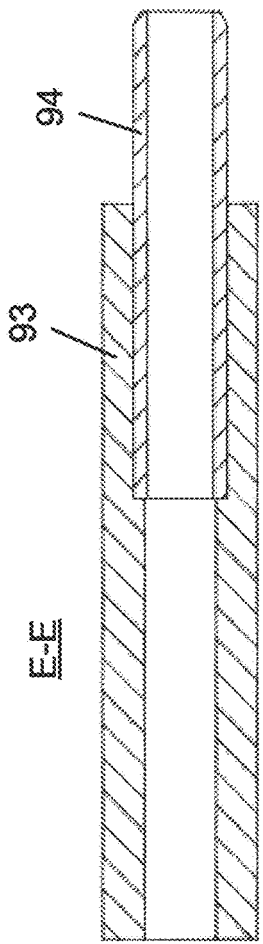
FIG. 18 is a cross sectional view of the cannula of FIG. 17, cut along plane E-E.

Alternatively, as shown in FIGS. 17 and 18, cannula 95 comprises tubular main body 93 connected with the hub, and a tubular secondary body 94 inserted within, and connected to, the inner surface of main body 93 by connection means including adhesion, laser welding, press fitting and threaded engagement. Material may be removed from the inner surface of main body 93 prior to connection thereto of secondary body 94. The outer surface of secondary body 93 may be surface treated with irregularities as described above.

FIGS. 19-23, 39-40 and 46-47 illustrate a second embodiment of the invention wherein the PBPI comprises a spring or any other suitable resilient means.

In the implementation of FIGS. 19-20, IO device 110 comprises a single-bodied tubular cannula 115 through the interior of which stylet shaft 6 longitudinally extends, and a helical compression spring 114 which is fit about cannula 105 and connected by connections means 112 such as laser welding and adhesion to the distal edge 117 of hub 22, and possibly also to cannula 115. Spring 114 is made of a biocompatible material or coated with a biocompatible material, and is shaped to form a completely smooth helical structure without any sharp discontinuities that would be injurious to a bodily part during a penetration procedure.

During the penetration procedure, pointed tip 7 penetrates soft tissue and then the proximal bone cortex. The distal portion 116 of spring 114 first contacts the proximal bone cortex, and then becomes compressed as tip 7 is penetrated deeper within the bone cortex towards the bone marrow cavity, in response to the increased resistance provided by the bone. The force applied by the health practitioner performing the penetration procedure is absorbed by the compressed spring 114, indicating to the health practitioner that the bone cortex has been penetrated. The health practitioner is then able to visualize the penetration site and to assess whether additional penetration is necessary.

The load imposed by the bone cortex increases during greater depth of penetration, resulting in a corresponding increase in spring deflection. Thus a greater force is required to be applied by the health practitioner in order to overcome the spring's compressive force and drive tip 7 to an even greater depth. Accordingly, this PBPI provides an indication as to depth of penetration as a function of spring resistance. A maximum depth of penetration may be controlled by a selected spring rate and by other mechanical characteristics of spring 114.

In the implementation of FIGS. 21-22, cannula 125 is configured similarly to cannula 55 of FIGS. 11 and 12, but with the addition of compression spring 124 and disc 127 having a slightly greater diameter than that of spring 124. Both spring 124 and disc 127 are freely fit over secondary body 63 of cannula 125. The proximal end of spring 124 is connected to step interface 79 by connections means 112, and the distal end of spring 124 is connected to disc 127 by similar connection means. Spring 124 becomes compressed when disc 127 contacts the bone cortex to provide an indication as to depth of penetration as a function of spring resistance. The indication of depth of penetration as a function of the spring resistance of spring 124 facilitates penetration of cannula 125 to a predetermined depth.

In the implementation of FIGS. 23A-D, IO device 130 comprises flexible tube 136 which is fit about single-bodied cannula 115 and connected by connections means 112 such as laser welding and adhesion to the distal edge 117 of hub 22, and possibly also to cannula 115. Stylet shaft 6 terminating with pointed tip 7 longitudinally extends through the hollow interior of cannula 115. Flexible tube 136 is formed with a plurality of longitudinally extending and circumferentially spaced slits 134 of limited length, e.g. one-fifth the length of flexible tube 136, adjacent to the flexible tube distal end 137, to provide a weakened tube region.

At the unloaded position of FIGS. 23A-B, flexible tube distal end 137 may be longitudinally aligned with cannula distal end 119. When IO device 130 becomes loaded after tip 7 penetrates the bone cortex, the reactive force applied by the bone is transmitted to IO device 130, causing flexible tube 136 to plastically deform as shown in FIGS. 23C-D, such that deformed flexible tube material 139 circumferentially adjacent a slit 134 expands radially outwardly from cannula 115 and flexible tube distal end 137 is caused to become proximally displaced with respect to cannula distal end 119 in response to the expansion forces resulting from the deformation.

Figure 39:
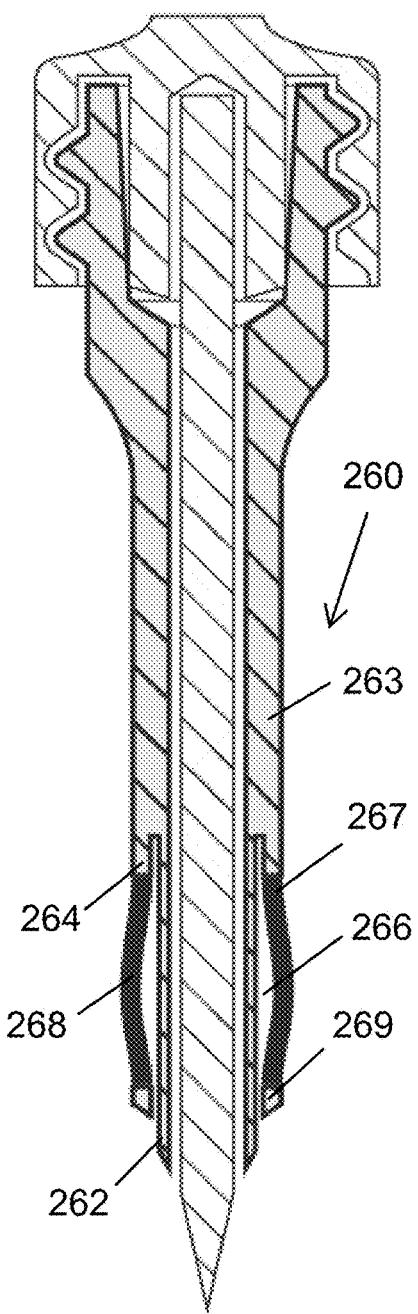
FIG. 39 is a longitudinal cross sectional view of an IO device according to another embodiment of the invention.
Figure 40:
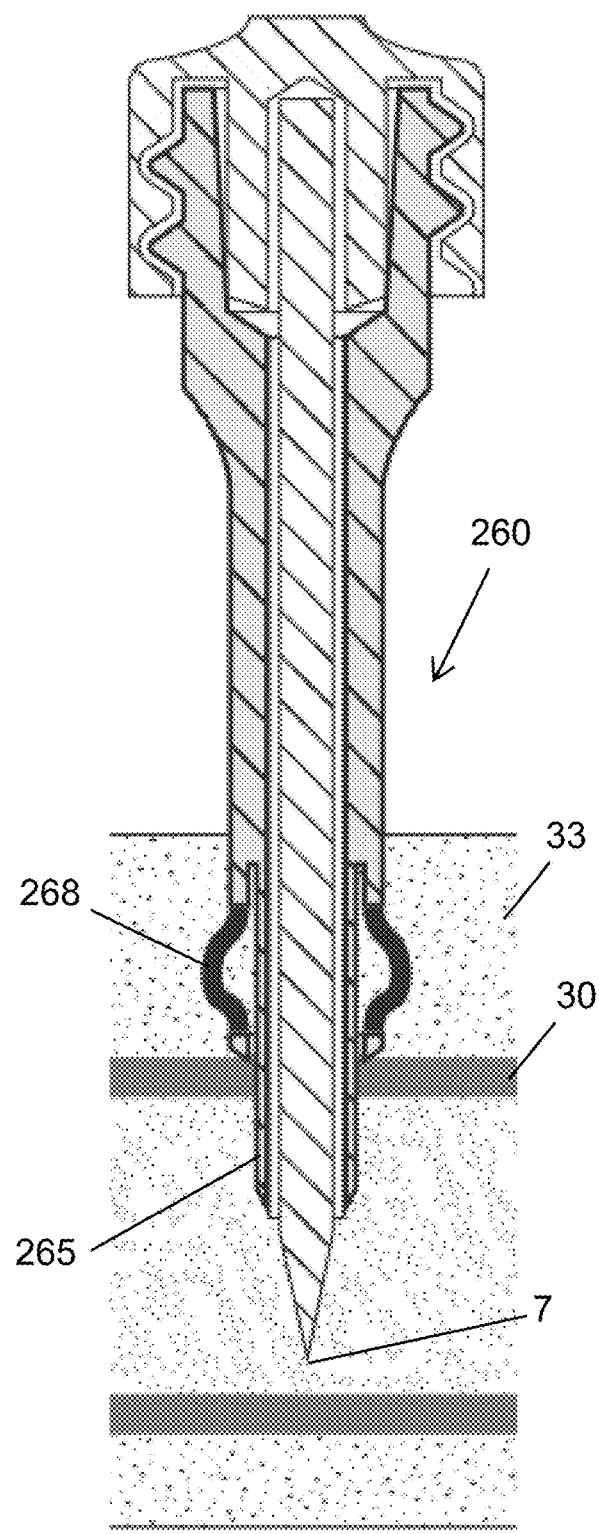
FIG. 40 is a longitudinal cross sectional view of the IO device of FIG. 39, shown following penetration of the bone cortex.

In the implementation of FIGS. 39-40, cannula 260 is configured with an annular recess 266 formed in metallic main body 263 to define a secondary cannula body 265 from its distal end 262 to an intermediate cannula region 264, which is spaced from stylet tip 7 by a distance that is not greater than 95% of the diameter of the bone marrow cavity or ranging from 1 mm to 30 mm. A biocompatible and resilient sleeve 268 having a length approximately equal to that of recess 266, for example made of rubber or plastic, is attached at its proximal end 267 to intermediate region 264 such as by welding while its distal end 269 is unattached. Although the sleeve distal end 269 is unattached to main body 263, the sleeve distal end is ensured of remaining in contact with secondary body 265, for example by being inserted with one or more rigid metallic elements.

During a penetration procedure shown in FIG. 40, a portion of sleeve 268 including distal end 269 is urged into the penetration site defined by stylet tip 7 and through soft tissue 33. Additional penetration of sleeve 268 through the penetration site is prevented when sleeve distal end 269 contacts proximal bone cortex 30. While sleeve distal end 269 remains in contact with proximal bone cortex 30, sleeve 268 plastically deforms proximally as an indication of initial penetration of secondary body 265 into the bone cortex. Sleeve 268 plastically deforms to a greatest extent when full penetration is achieved and intermediate region 264 is located at a minimal distance to sleeve distal end 269, and thus functions as a stopper.

It will be appreciated that secondary body 265 may be additionally configured with a roughened surface to constitute an additional PBPI.

Figure 46:
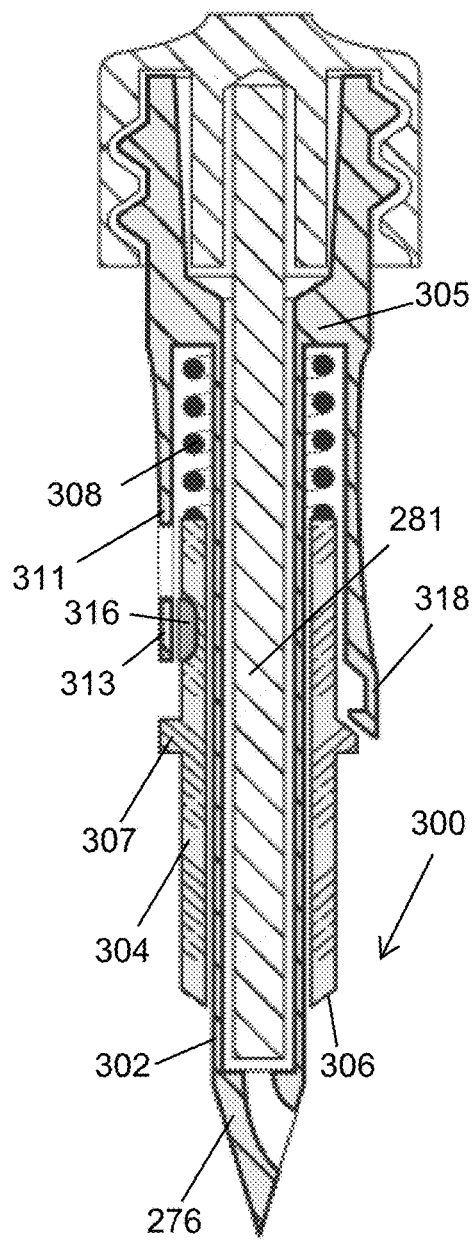
FIG. 46 is a longitudinal cross sectional view of an IO device according to another embodiment of the invention.
Figure 47:
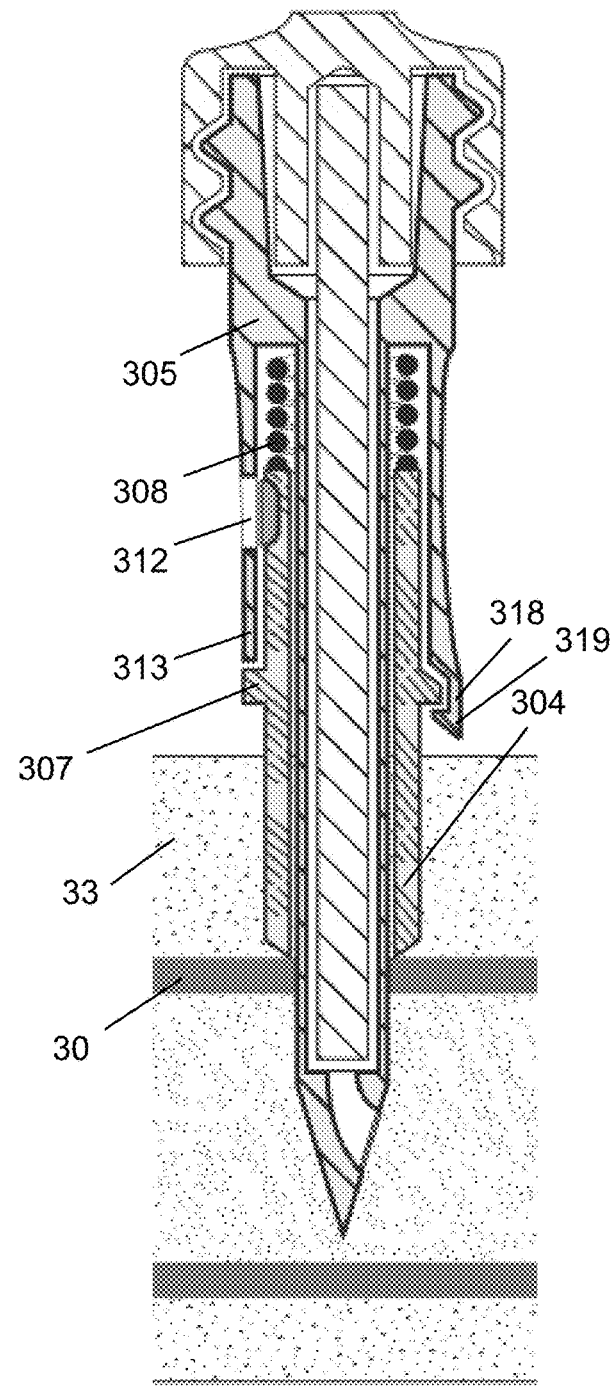
FIG. 47 is a longitudinal cross sectional view of the IO device of FIG. 46, shown following penetration of the bone cortex.

In the implementation of FIGS. 46-47, cannula 300 comprises a thin-walled cylinder 302 providing the secondary body that is integrally formed with needle element 276, a reinforcing post 281 inserted within the interior of cylinder 302 which coincides with the bore of hub 305, and a thicker-walled rigid sleeve 304 fixedly attached to cylinder 302 to define the step interface 306. Sleeve 304 is configured with an abutment 307 extending radially outwardly from its outer surface. A helical spring 308, which is received in a spring housing surrounding a proximal portion of cylinder 302 that is adjacent to hub 305 and that is positioned radially inwardly to a wing element 311 extending distally from hub 305, is attached at its distal end to the proximal end of sleeve 304 and at its proximal end to hub 305. The spring force of spring 308 is selected to be greater than the resistance of soft tissue 33 but less than the resistance of bone cortex 30.

To reinforce thin-walled secondary body 302 during penetration into soft tissue and to resist flexure or breakage thereof as a result of the moment that is manually applied during bone penetration, truncated solid-core post 281 is inserted within the interior of the thin-walled secondary body. Reinforcement of the thin-walled secondary body 302 is made possible when the radial clearance between post 281 and secondary body 302 is no more than 150 microns, and may even be non-existent while post 281 is in abutting relation with secondary body 302. The truncated solid-core post is advantageous in that it is assured of not penetrating the bone marrow cavity and therefore is assured of not transmitting diseases that are communicable upon access to the bone marrow cavity, when removed from the cannula. Also, the truncated post, as opposed to one that is pointed, prevents a risk of a needlestick injury to the health practitioner as a result of an unintentional puncturing of the skin.

Prior to the penetration procedure as shown in FIG. 46 when spring 308 is in a relaxed state, the distal end 313 of wing element 311 is proximally spaced from abutment 307 and conceals visually indicative element 316 attached to or imprinted on a specific location on sleeve 304, and which may be provided with different colors. Also, detent 318, which may be configured as a depression formed in a thickened appendage at a distal region of wing element 311 and substantially complementary to the cross section of abutment 307, is slightly proximally spaced from abutment 307.

During a penetration procedure shown in FIG. 47, spring 308 does not compress when needle element 276 passes through soft tissue 33, but is compressed when needle element 276 initially penetrates bone cortex 30. In response to the compression of spring 308, hub 305 is displaced distally relative to sleeve 304, until detent 318 engages with abutment 307 with an audible snapping sound serving as an PBPI following plastic deformation of the flexible distal contact element 319 and the remaining distal end 313 of wing element 311 is able to contact abutment 307. As a result of the distal displacement of wing element 311, visually indicative element 316 is readily visualized through window 312 formed in wing element 311 to constitute a PBPI.

Wing element 311 may be calibrated such that visually indicative element 316 is centered in window 312 when bone cortex 30 is fully penetrated and step interface 306 engages the outer side of bone cortex 30, causing spring 308 to be fully compressed and detent 318 to be snapped onto abutment 307. Visually indicative element 316 may be non-centered upon initial contact between needle element 276 and bone cortex 30, when spring 308 is not fully compressed.

It will be appreciated that secondary body 302 may be configured with a roughened surface to constitute an additional PBPI.

FIGS. 41-45 illustrate a third embodiment of the invention wherein the cannula comprises a first PBPI embodied by a resilient element and a second PBPI embodied by a visually indicative element or a non-roughened tactile element. A stopper such as a step interface may also be provided, and the step interface may be constituted in part by a thin-walled secondary body member. The secondary body member is reinforced with a truncated post as described in FIG. 46.

In the implementation of FIGS. 41-43, a radial recess is formed at the distal end of the metallic main body 272 of cannula 270 to define thin-walled secondary body 274 and a step interface 292. Main body 272 is integral with, or connected to, proximal hub 275, which is configured with internal cavity 284 in communication with central bore 273 and with outer threading 279.

Thin-walled secondary body 274 is reinforced by truncated solid-core post 281, which is inserted within the central bore 273 of cannula 270 at a close proximity to secondary body 274. Post 281 has a head element 280, which includes elements for coupling with cannula hub 275, visually indicative element 283, as well as a window 286 for visualizing visually indicative element 283. The coupling elements include a hub 288, which is insertable within internal cavity 284 of cannula hub 274, and an integral outer hand graspable element 285, which is radially spaced from post hub 288 and has inner threading 289 for engagement with outer threading 279 of cannula hub 274. Visually indicative element 283, generally provided with different colors, extends proximally from post hub 288 to a central element 287, and is normally concealed by threading 279 of cannula hub 275.

Secondary body 274 is closed, and terminates with an integral pointed needle element 276 used to perform a penetration procedure. A side inclined surface 277 of needle element 276 is configured with a relatively large opening 278 at a terminal end of a non-linear passageway 271 formed within the solid core of needle element 276 and proximal to tip 279, through which infusion fluids and other medications are flowable to the blood marrow cavity of a target bone.

A resilient sleeve 282 is connected at one axial end to step interface 292 and to needle element 276 at the other axial end. Prior to the penetration procedure, as shown in FIG. 41, sleeve 281 is in a tensed condition, being in contact with secondary body 274 while step interface 276 is significantly spaced from needle element 276.

During a penetration procedure, as shown in FIG. 42, needle element 276 is caused to penetrate soft tissue 33 and proximal bone cortex 30 by holding element 285 and rotating cannula hub 275 while inner threading 289 continues to be engaged with outer threading 279. Expansion of sleeve 282 due to the greater resistance of bone cortex 30, to which needle element 276 has penetrated, constitutes the first PBPI. As a result of the expansion of sleeve 282, step interface 292 is caused to be brought closer to needle element 276. Visually indicative element 283 serving as the second PBPI is no longer concealed by outer threading 279 of cannula hub 275, and is able to visualized through window 286

Figure 44:
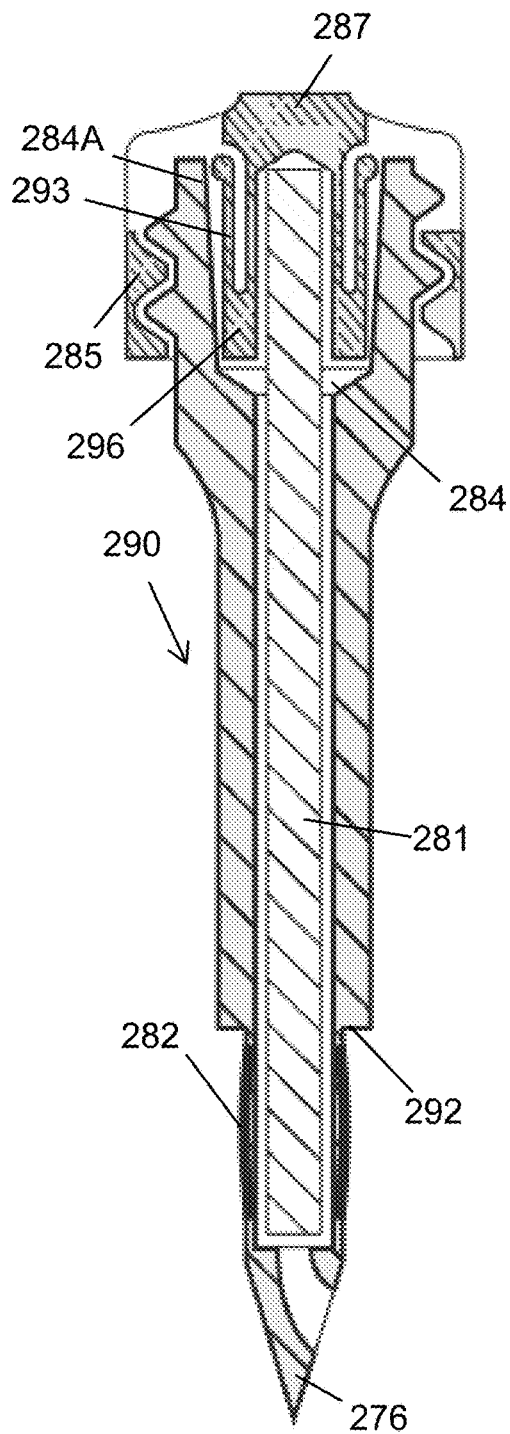
FIG. 44 is a longitudinal cross sectional view of an IO device according to another embodiment of the invention.
Figure 45:
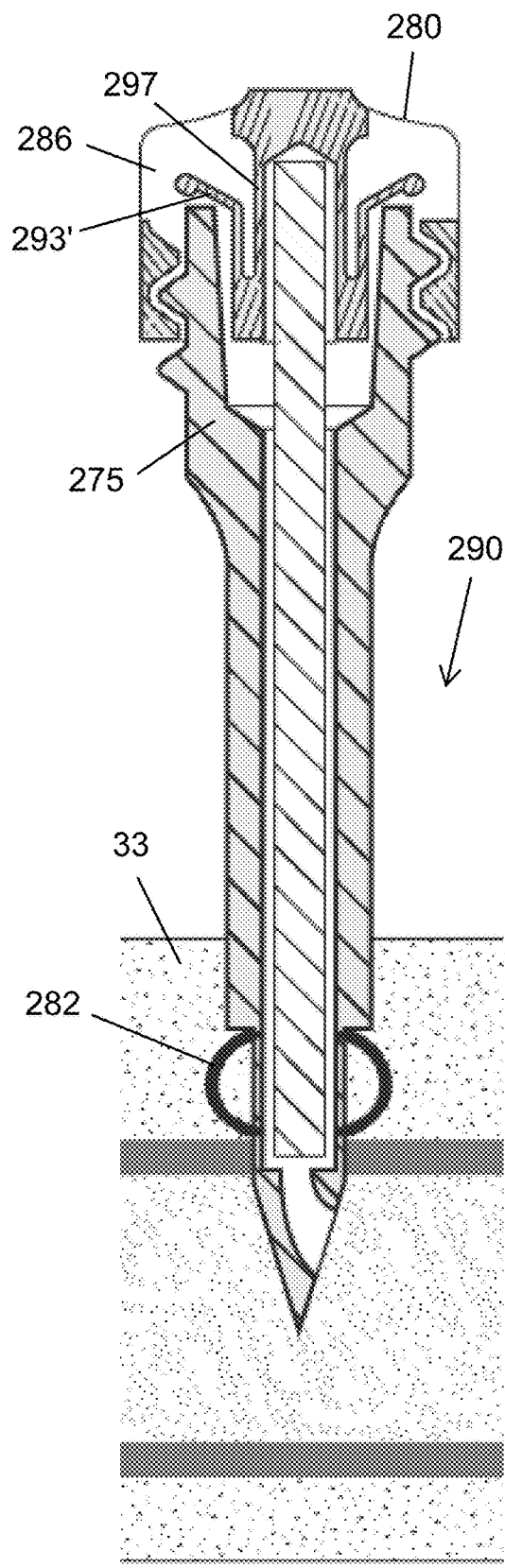
FIG. 45 is a longitudinal cross sectional view of the IO device of FIG. 44, shown following penetration of the bone cortex.

Cannula 290 of FIGS. 44-45 is configured similarly to cannula 270 of FIGS. 41-43, with the exception of the second PBPI. In this implementation, the second PBPI is a flexible element 293 such as a leaf spring that is biased to extend radially to an outer region of head element 280. A distal portion of flexible element 293 extends upwardly from the outermost region of annular post hub 296 that is integrally formed with outer hand graspable element 285 and that is connected to central element 287 located above post 281 by rigid circumferentially extending band 297. Prior to the penetration procedure as shown in FIG. 44 when sleeve 282 is in a tensed condition, flexible element 293 is radially restrained and concealed by the wall 284A of hub cavity 284, and is therefore concentric with, and positioned at substantially the same height as, band 297. During a penetration procedure shown in FIG. 45, sleeve 282 expands and hub 275 is caused to be brought closer to needle element 276. A proximal portion 293' of the flexible element is no longer restrained, and therefore achieves the illustrated radially extended configuration. This radially extended configuration is readily visualized through window 286 to constitute a PBPI. The radially extended flexible element 293 may also provide tactile feedback by vibrating during sudden outward radial expansion after ceasing to be restrained in response to the distal displacement of wall 284A.

Resilient sleeve 282 is configured not to deform while penetrating soft tissue 33, thus allowing step interface 292 to also penetrate the soft tissue as well. Additional penetration of needle element 276 is prevented when sleeve 282 is fully compressed and step interface 292 is minimally spaced from the bone cortex.

FIGS. 24-26 illustrate a fourth embodiment of the invention wherein the PBPI comprises a frictionally engageable element.

Figure 24A:
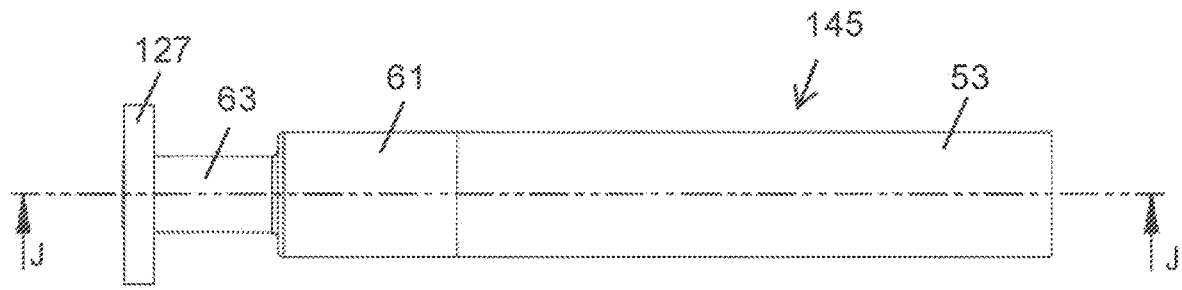
FIG. 24A is a side view of a cannula according to another embodiment of the invention, shown in an unloaded position.
Figure 24B:
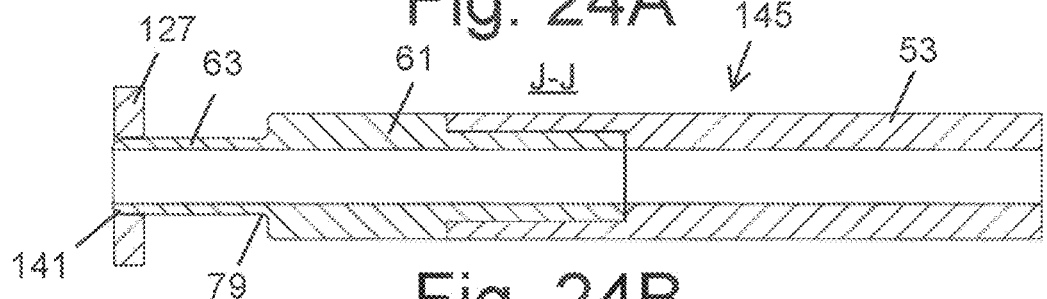
FIG. 24B is a cross sectional view of the cannula of FIG. 24A, cut along plane J-J.
Figure 24C:
FIG. 24C is a side view of the cannula of FIG. 24A, shown in a loaded position.
Figure 24D:
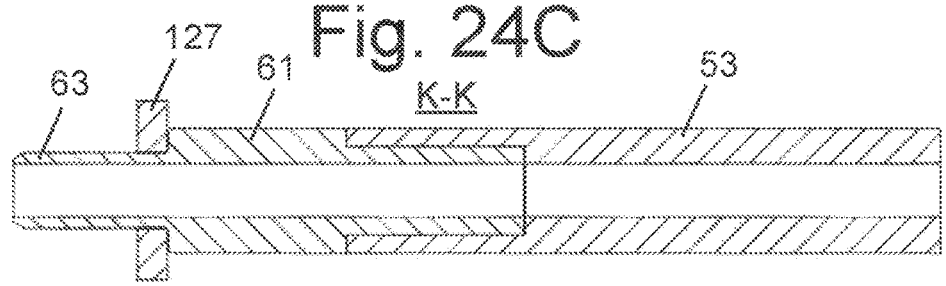
FIG. 24D is a cross sectional view of the cannula of FIG. 24C, cut along plane K-K.
Figure 25A:
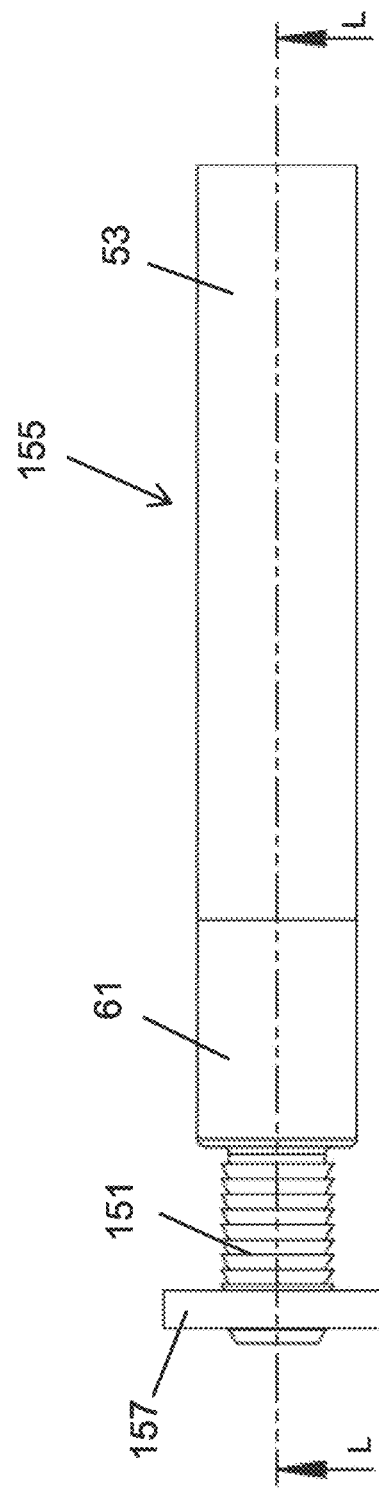
FIG. 25A is a side view of a cannula according to another embodiment of the invention, shown in an unloaded position.
Figure 25B:
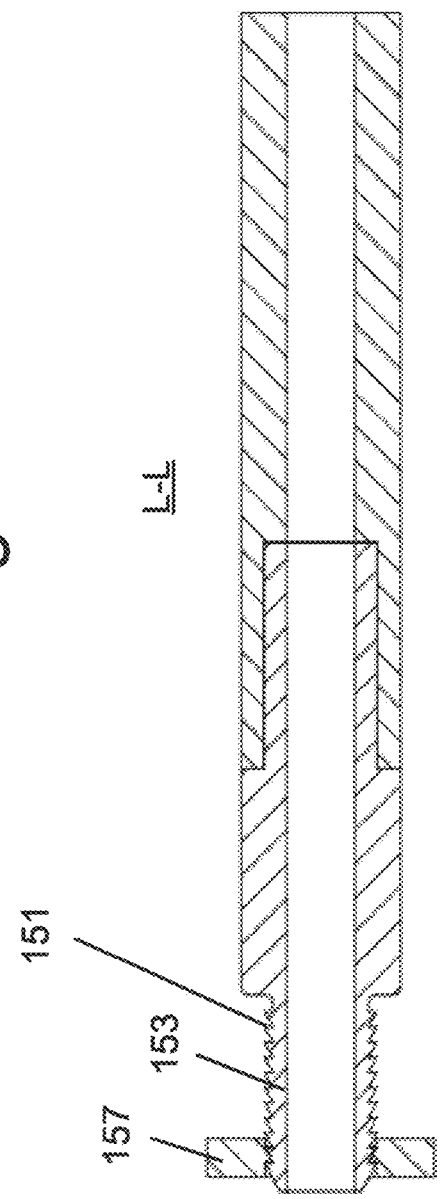
FIG. 25B is a cross sectional view of the cannula of FIG. 25A, cut along plane L-L.
Figure 25C:
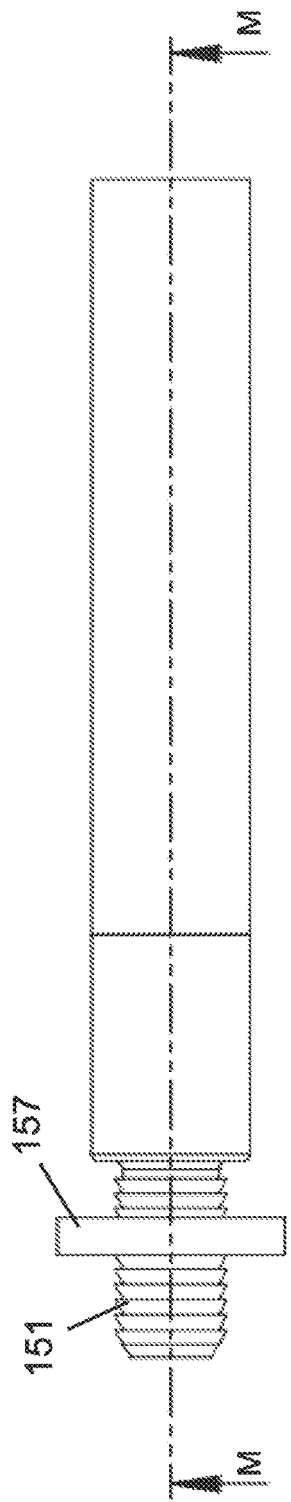
FIG. 25C is a side view of the cannula of FIG. 25A, shown in a loaded position.
Figure 25D:
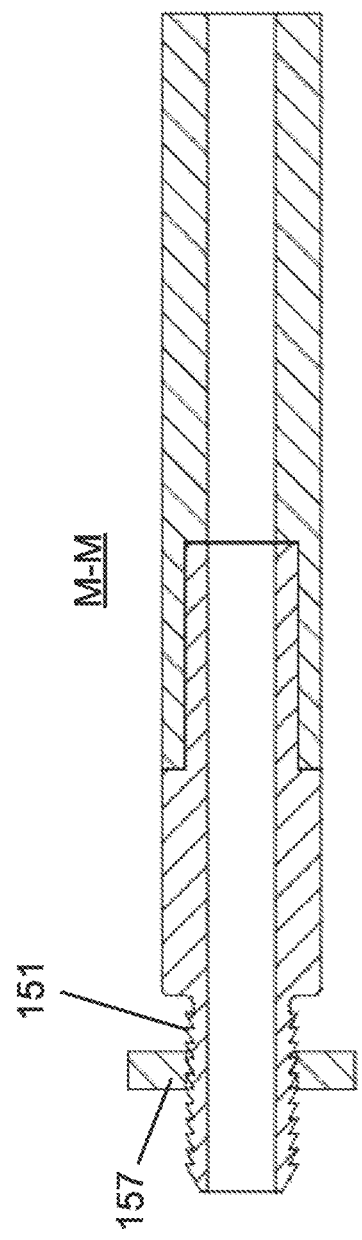
FIG. 25D is a cross sectional view of the cannula of FIG. 25C, cut along plane M-M.

In the implementation of FIGS. 24A-D, cannula 145 is configured similarly to cannula 125 of FIG. 21, but without the compression spring. Disc 127 is mounted on, and frictionally engaged with, secondary body 63 of cannula 145, so as to be aligned with distal end 141 of secondary body 63 in an unloaded condition, as shown in FIGS. 24A-B. Disc 127 is caused to be proximally displaced along secondary body 63 in response to contacting the bone cortex during a penetration procedure, until being limited by step interface 79, as shown in FIGS. 24C-D, while a tactile indication of the frictional engagement between disc 127 and secondary body 63 and therefore of the bone penetration is transmitted to the health practitioner.

Disc 127 may be configured such that its distal end is narrow, and may even be pointed to a certain extent, while its proximal end progressively widens, similarly to a triangular pyramid, in order to enable relatively effortless penetration into the soft tissue. Such a disc configuration is also suitable for cannula 125 of FIGS. 21-22.

In the implementation of FIGS. 25A-D, cannula 155 is configured similarly to cannula 145 of FIGS. 24A-D; however, secondary body 153 is configured with a plurality of serrated ribs 151 that are engageable with disc 157 to facilitate the longitudinal displacement of the latter in response to the bone penetration. A depth of penetration may be controlled during the gradual displacement of disc 157.

Disc 157 may be configured such that its distal end is narrow, and may even be pointed to a certain extent, while its proximal end progressively widens, similarly to a triangular pyramid, in order to enable relatively effortless penetration into the soft tissue.

In the implementation of FIGS. 26A-B, IO device 170 comprises a longitudinally bored frustoconical element 174 that is secured to single bodied cannula 115 by adhesion, laser welding or by a press fit, through the interior of which stylet 6 longitudinally extends. Frustoconical element 174, which may be made of a rigid material such as plastic or metal, or a flexible material such as silicon or rubber, is secured to cannula 115 such that its widest portion 176 is proximally oriented, so as to complete a conical shape together with pointed tip 7 of stylet 6. The provision of frustoconical element 174 increases the resistance of the bone cortex following bone penetration by pointed tip 7, and also facilitates sealing of the penetration site.

The stopper may be configured in other ways as well.

Figure 33:
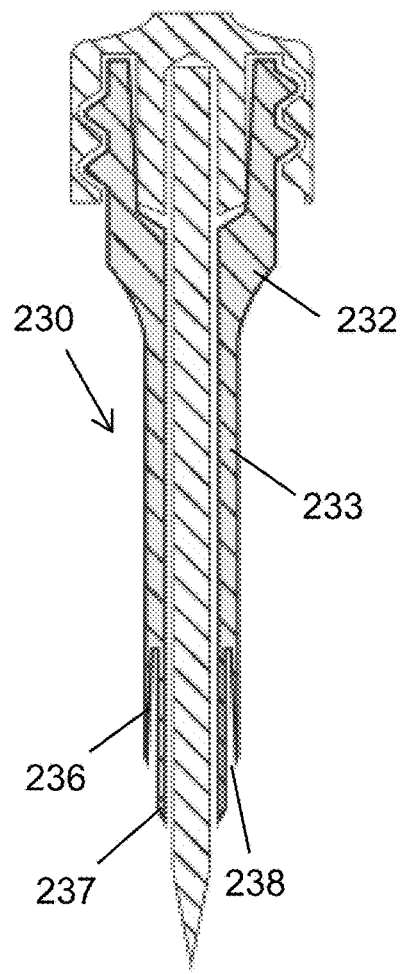
FIG. 33 is a longitudinal cross sectional view of an IO device according to another embodiment of the invention.
Figure 34:
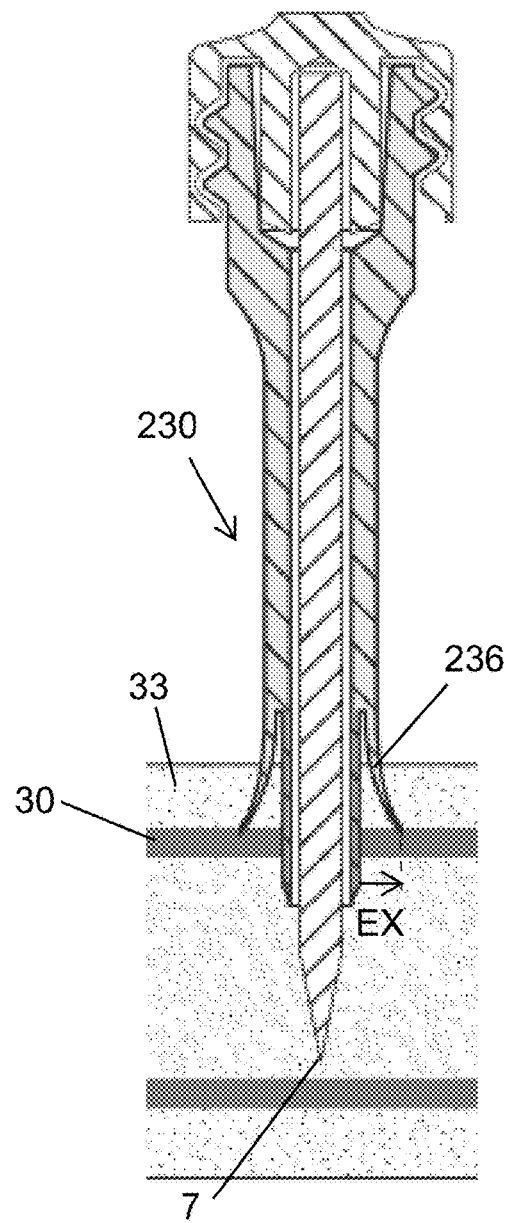
FIG. 34 is a longitudinal cross sectional view of the IO device of FIG. 33, shown following penetration of the bone cortex.

As shown in FIGS. 33 and 34, the stopper of tubular cannula 230 is configured as a plurality of circumferentially spaced, radially expandable leaves 236. Each leaf 236 is defined by a longitudinal slit 238 formed in the main body 233, which is connected to, or integral with, and extending distally from, hub 232. A secondary body 237 concentric to, and of a smaller outer diameter than, main body 233 is produced, following formation of the slits 238. The entire outer surface of secondary body 237 may be roughened to constitute the PBPI, or alternatively only the portion of secondary body 237 which is distal to the leaves 236 may be surface roughened.

The leaves 236 are sufficiently long, e.g. on the order of 2 mm, to undergo appreciable radial expansion when caused to contact the proximal bone cortex 30 during an IO penetration procedure, following penetration of the overlying soft tissue 33. The radial expansion is preferably limited to a radial dimension EX of approximately 1 mm from the secondary body 237, so that the tactile feedback received upon engagement of each expanded leaf 236 with the proximal bone cortex 30 will be increased and the overpenetration of stylet tip 7 will be prevented.

Figure 35:
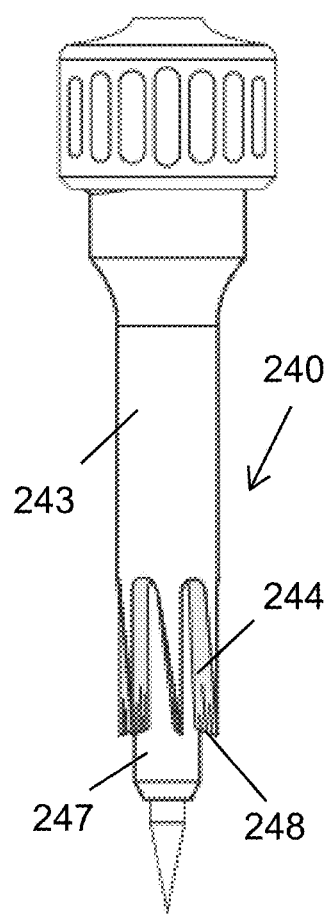
FIG. 35 is a side view of an IO device according to another embodiment of the invention.
Figure 37:
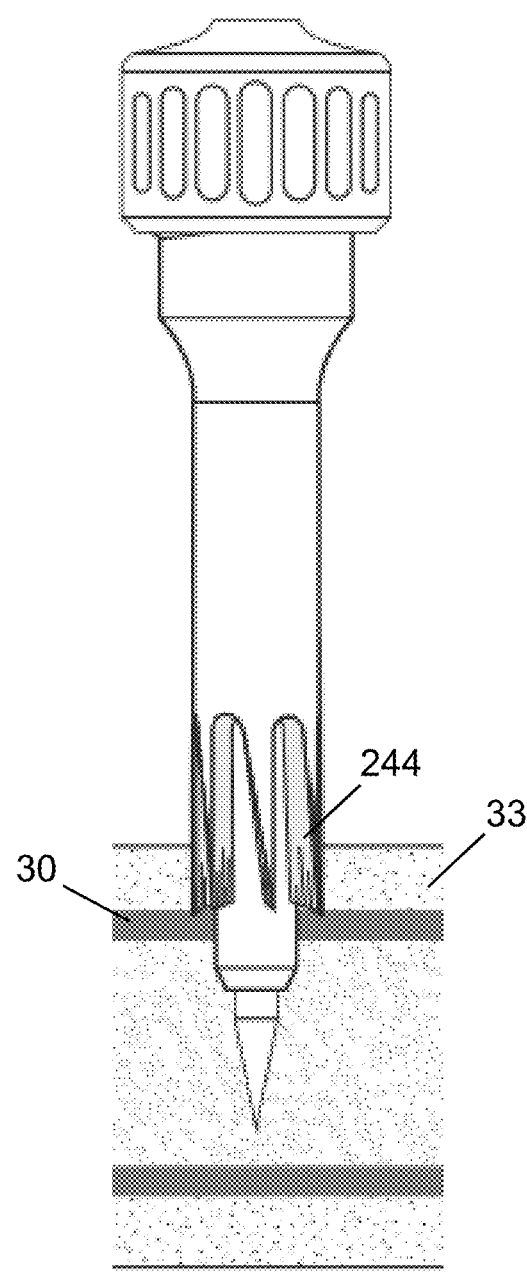
FIG. 37 is a side view of the IO device of FIG. 35, schematically shown following penetration of the bone cortex.
Figure 36:
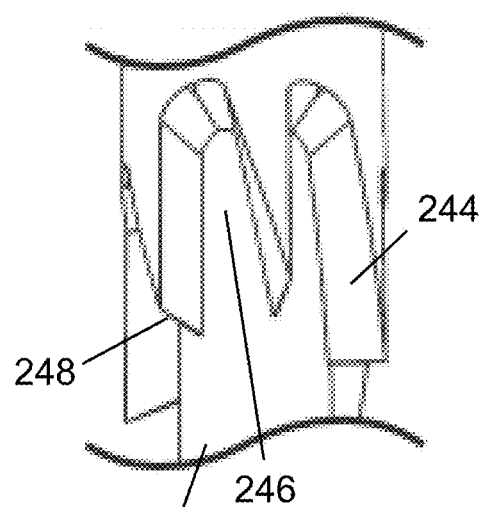
FIG. 36 is a perspective view from the side of a plurality of integral scalpel blades used in conjunction with the device of FIG. 35.

Cannula 240 illustrated in FIGS. 35-37 is configured with a plurality of integral metallic scalpel blades 244, assisting in penetrating soft tissue 33 overlying the proximal bone cortex 30 and functioning as a stopper. The metallic tubular main body 243 is machined during a material removal operation, such as by CNC, to define the blades 244 which protrude radially outwardly from secondary body 247, as well as a void region 246 located between circumferentially adjacent scalpel blades 244. Each scalpel blade 244 terminates with a sharpened and widened distal surface 248, which is configured to contact the proximal bone cortex 30 during a penetration procedure, as shown in FIG. 37, resulting in a substantial increase in resistance to additional penetration. The entire outer surface of secondary body 247 may be roughened to constitute the PBPI, or alternatively only the portion of secondary body 247 which is distal to the widened and sharpened surfaces 248 may be surface roughened.

Cannula 240 may also be made of a plastic material, such as injection molded plastic, and is integral with hub 258.

FIGS. 38A-D illustrate IO injection PBPI-associated cannulas that facilitate side tubulation. As cannulas through which infusion tubes pass generally protrude perpendicularly from a limb following an IO penetration procedure, a significant risk exists of cannula detachment from the penetration site exists due to accidental impact with the relatively long protruding length of the cannula. Also, the infusion tubes are caused to bend so that they will be attached to the limb and immobilized, leading to reduced flow of the infusion fluid. These problems are obviated with the use of the side-tubulation cannulas.

In the implementation of FIGS. 38A-B, side-tubulation cannula 350 is of the two-way stopcock type. Cannula 350 has a main body 352 within the central bore 353 of which stylet 6 for initiating penetration of proximal bone cortex 30 is insertable, the stylet passing through sealing element 358 provided in cavity 354 formed in hub 355 which is integral with main body 352. A slotted end cap 359 fixedly engaged with stylet 6 is used to occlude cavity 354 and also to transmit torque to the stylet. Main body 352 is recessed to define a thin-walled secondary body 356 and a step interface 357, and is further configured with an integral perpendicularly extending side body 361, which is configured with a side bore 364 in fluid communication with central bore 353, configured to be occluded by plug 366 insertable therewithin. For ease in manipulation, plug 366 has a cap 367 that is threadedly engageable with outer threading 362 provided in side body 361.

The health practitioner is assisted by the one or more PBPIs during a penetration procedure to indicate that the penetration procedure should be terminated upon initial penetration into the proximal bone cortex. One PBPI may be a roughened surface 363 formed on secondary body 356. Another PBPI may be a schematically illustrated visually indicative element 368 according to any embodiment described herein when hub 355 is adapted to house the visually indicative element and other means cooperating therewith. Another PBPI may be step interface 357.

Following the penetration procedure, stylet 6 is removed. The health practitioner can connect any standard extension set or syringe to hub 355 or to outer threading 362 in order to inject fluid through bores 353 into the bone marrow cavity, while sealing element 358 seals cavity 354.

In the implementation of FIGS. 38C-D, side-tubulation cannula 370 has a block 371 shaped to define main body 372 having one straight edge 373 and one curved edge 374, tubular thin-walled secondary body 376, step interface 377 and side body 383 positioned at the terminal end of curved edge 374. Side bore 384 is formed in side body 383, and curved bore 379 in communication with side bore 384 is formed in main body 372, secondary body 376, and side body 383. Curved stylet 386, which is slightly flexible or made of a shape memory material such as Nitinol, is adapted to be inserted within curved bore 379. Slotted plug 388 fixedly engaged with stylet 386 is used to occlude side bore 384 and also to transmit torque to the stylet.

The health practitioner is assisted by the one or more PBPIs during a penetration procedure to indicate that the penetration procedure should be terminated upon initial penetration into the proximal bone cortex. One PBPI may be a roughened surface 381 formed on secondary body 376. Another PBPI may be a schematically illustrated visually indicative element 387 according to any embodiment described herein when side bore 384 is adapted to house the visually indicative element and other means cooperating therewith. The health practitioner may also be assisted by a stopper such as step interface 377.

Following the penetration procedure, stylet 386 is removed and an infusion tube is inserted through curved bore 379 into the bone marrow cavity.

Figure 48:
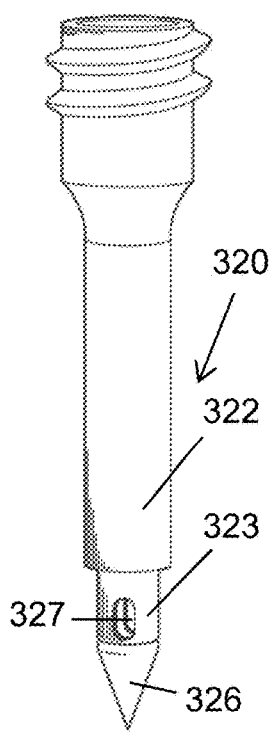
FIG. 48 is a perspective view from the side of an IO device according to another embodiment of the invention.

FIGS. 48-49 illustrate a cannula 320 which is configured with a thin-walled secondary member 323 defining a step interface, which is reinforced by an insert 325, generally tubular, which is integrally formed with a solid needle element 326 of triangular cross section. Insert 325 is placed in contact with, and welded to, the wall 331 of central bore 334 extending continuously through main body 322 and secondary body 323, and is longer than secondary body 323. Thin-walled secondary member 323 is suitably reinforced by insert 325 when the combined thickness of secondary member 323 and insert 325 is at least 0.2 mm. One or more apertures 327 are formed in both secondary body 323 and insert 325 to facilitate discharge of infusion fluids and medication into the bone marrow cavity.

Figure 50:
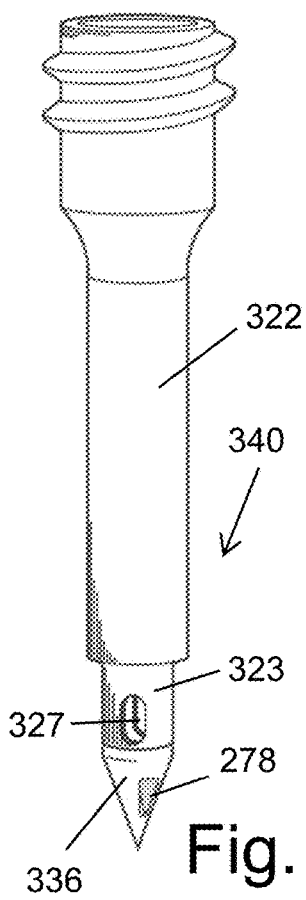
FIG. 50 is a perspective view from the side of an IO device according to another embodiment of the invention.
Figure 51:
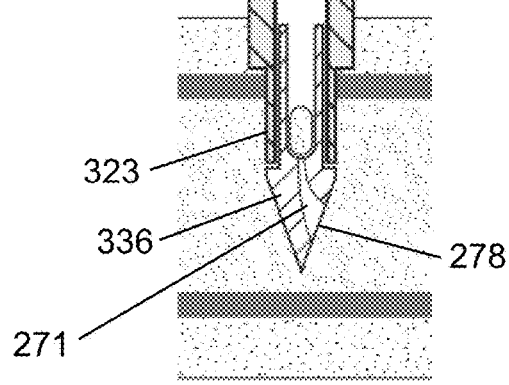
FIG. 51 is a longitudinal cross sectional view of the IO device of FIG. 50, shown following penetration of the bone cortex.

FIGS. 50-51 illustrate a cannula 340 which is configured similarly to cannula 320 of FIG. 48, but additionally formed with a non-linear passageway 271 provided within the solid core of needle element 336 and terminating with opening 278, as also illustrated in FIG. 41.

Although not shown, cannula 320 and 340 may each be configured with any one or more types of PBPI described herein.

In any of the embodiments described hereinabove, where relevant, the distal end of the PBPI may be aligned with the pointed end of the stylet.

In any of the embodiments described hereinabove, where relevant, the distal open end of a cannula 185 shown in FIG. 27 (for example about which is fit compression spring 114 of FIG. 19) may be configured with serrations 187 adapted to penetrate a bone cortex in addition to or in replacement of a stylet, or the distal closed and pointed end of a cannula 195 for penetrating a bone cortex upon being rotated, e.g. conically shaped, shown in FIG. 28 (for example about which is fit compression spring 114 of FIG. 19) may be configured with an aperture 198 through which an infusion fluid is able to be discharged via the penetration site to the blood marrow cavity.

In any of the embodiments described hereinabove, the cannula may be stabilized, primarily for use during performance of an IO penetration procedure in conjunction with bones of relatively low density, such as the sternum or bones of an infant.

An exemplary IO device 210 illustrated in FIGS. 29-32 may be used to stabilize a cannula according to any of the embodiments described herein during performance of an IO penetration procedure.

Figure 29:
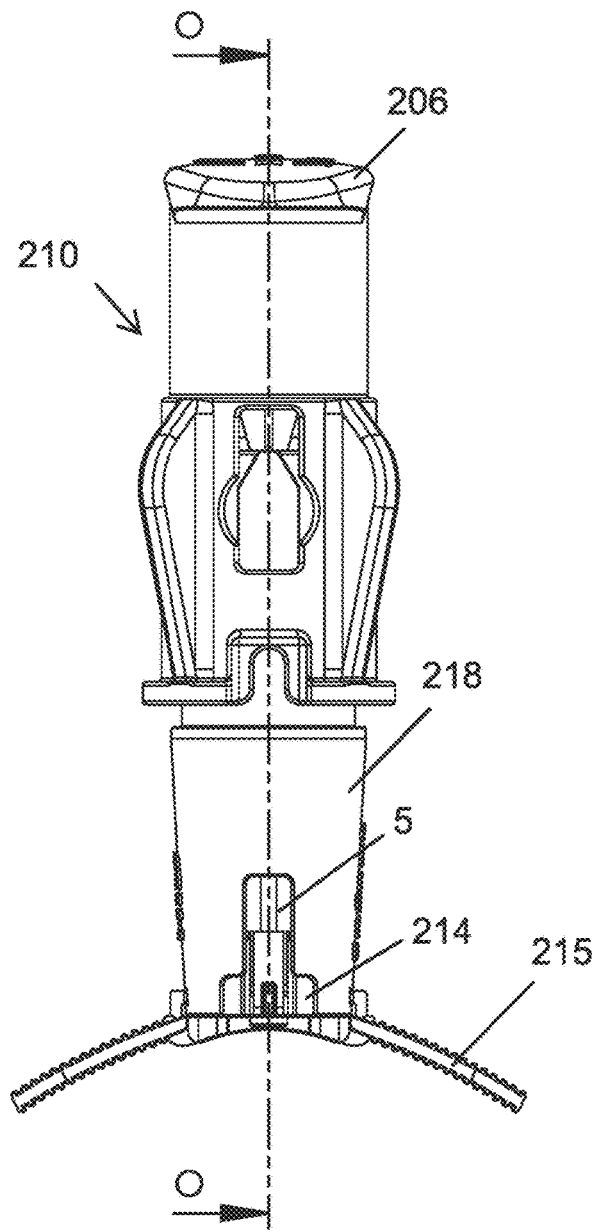
FIG. 29 is a side view of a stabilizing IO device according to another embodiment of the invention, showing the cannula secured thereby in a pre-penetration position.
Figure 30:
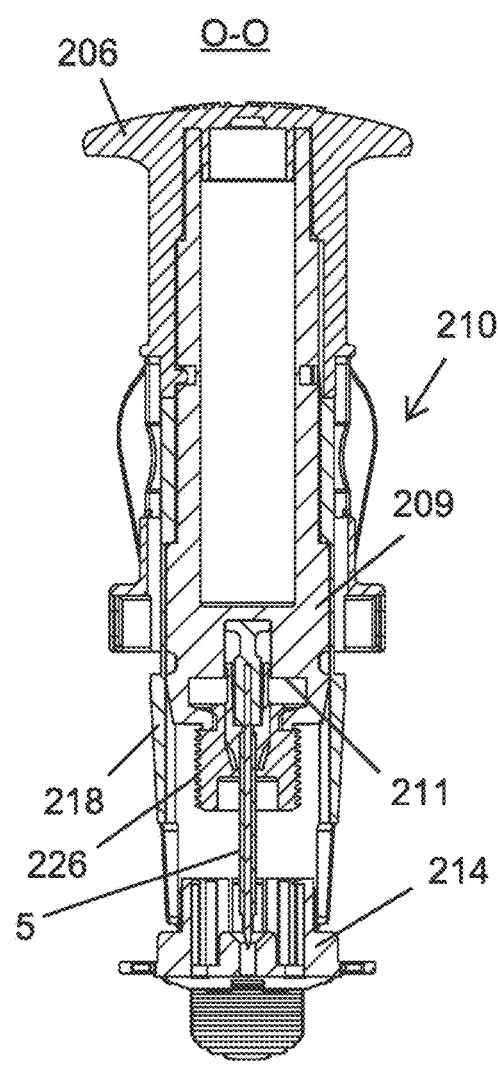
FIG. 30 is a cross sectional view of the IO device of FIG. 29, cut along plane O-O.

FIGS. 29-30 illustrate IO device 210 when cannula 5 secured thereby is in a pre-penetration position. FIGS. 31-32 illustrate IO device 210 when cannula 5 is in a post-penetration position.

IO device 210 comprises an outward and proximal safety cap shell 206, a solid force transmitter 209 connected internally to safety cap shell 206, an annular stabilizer 214 distally spaced from the distal edge 211 of force transmitter 209 and provided with two outwardly extending wing elements 215 for engaging a skin surface adjacent to a penetration site, and an annular interface member 218 releasably coupling safety cap shell 206 to stabilizer 214 and enclosing cannula 5 and force transmitter 209. The outer periphery of stabilizer 214 is defined by a plurality of circumferentially spaced and vertically oriented border elements 216, each of which has a proximal engagement element 219 that is substantially perpendicular to the corresponding border element and extends slightly radially inwardly therefrom.

The hub 22 of cannula 5 is fixedly secured to a dedicated cavity formed in a needle housing 224 of circular cross section when in the pre-penetration position. Needle housing 224 is configured with a plurality of vertically spaced and circumferentially extending inclined ratchet teeth 226 and with a proximal neck 225 having a larger diameter than teeth 226. Neck 225 is engaged by flexible engagement legs 212 extending downwardly and radially inwardly from distal edge 211 of force transmitter 209, when needle housing 224 is in the pre-penetration position. A plug 227 releasably and internally secured to hub 22 is positioned within dedicated cavity 217 formed within force transmitter 209 and proximally spaced from distal edge 211 thereof. In the pre-penetration position, interface member 218 is locked in position and cannula 5, together with stylet 6, is prevented from being distally displaced due to the inability of force transmitter 209 of being displaced.

Upon rotating safety cap shell 206 approximately 90 degrees, interface member 218 becomes decoupled from safety cap shell 206. A distal force then applied to safety cap shell 206 causes needle housing 224 to be distally displaced until ratchet teeth 226 are engaged by the plurality of engagement elements 219 of stabilizer 214 in the post-penetration position. The penetration procedure is also assisted by rotation of safety cap shell 206, to cause rotation of stylet 6 within the bone cortex. Upon subsequent proximal displacement of safety cap shell 206, neck 225 of needle housing 224 becomes disengaged from flexible engagement legs 212. Stabilizer 214 and needle housing 224 remain at the penetration site, and safety cap shell 206 and interface member 218 are able to be removed therefrom. Plug 227 is removed from hub 22 in order to infuse liquids into the bone marrow cavity.

While some embodiments of the invention have been described by way of illustration, it will be apparent that the invention can be carried out with many modifications, variations and adaptations, and with the use of numerous equivalents or alternative solutions that are within the scope of persons skilled in the art, without exceeding the scope of the claims.

The invention claimed is:

1. A cannula for use in a terminable intraosseous device to indicate penetration of a cortex of a target bone, comprising:
    a) a cannula body;
    b) a penetrator-independent proximal bone penetration indicator (PBPI) associated with said cannula body for positively indicating initial penetration into said proximal bone, said PBPI comprising a roughened surface provided at a distal end of an outer surface of said cannula body without abruptly increasing an outer diameter of said cannula body, to assist in increasing an amplitude of vibrations that are generated immediately upon contact with a bone cortex of said proximal bone during performance of an intraosseous injection; and
    c) a stopper engageable with the bone cortex of said proximal bone, for preventing additional penetration, in addition to a given penetration depth to which said cannula body has been penetrated, into said proximal bone,
    wherein said roughened surface and said stopper constitute two distinct types of direct penetrator-independent tactile feedback during performance of the intraosseous injection into the proximal bone.

2. The cannula according to claim 1, wherein the stopper comprises one or more mechanical vibration intensifiers associated with the cannula body, in addition to the roughened surface, for increasing an amplitude of vibrations that are generated upon contact with the bone cortex during performance of the intraosseous injection.

3. The cannula according to claim 1, wherein the cannula body is a tubular body which comprises a main body and a secondary body distal to said main body, said main body being of a larger outer diameter than said secondary body, and the stopper is a step interface interfacing between said main and secondary bodies, positioned proximally to the roughened surface and defining a second vibration intensifier, wherein said secondary body is configured with the roughened surface to define a first vibration intensifier for generating vibration intensification immediately upon contacting the bone cortex.

4. The cannula according to claim 3, wherein the cannula body defines a lumen within which a stylet is insertable and for securely engaging a shaft of said stylet, when inserted within said lumen, wherein said lumen extends continuously and at a uniform bore diameter between the main and secondary tubular bodies.

5. The cannula according to claim 3—
    a) which is integrally formed with the main and secondary tubular bodies; or
    b) wherein the secondary tubular body is attachable to the main tubular body; or
    c) wherein the secondary tubular body is releasably attachable to the main tubular body; or
    d) wherein the main tubular body is attachable to the secondary tubular body.

6. The cannula according to claim 3, wherein—
    a) the radial protrusion of the step interface relative to an outer diameter of the secondary body is at least 0.1 mm; or
    b) the radial protrusion of the step interface relative to an outer diameter of the secondary body ranges from 0.1 to 3.0 mm; or
    c) the step interface is spaced from a tip of the stylet, when inserted within the lumen of the cannula, by a dimension that is no greater than 95% of a diameter of the marrow cavity of a target bone; or
    d) the step interface is spaced from the stylet tip by a dimension ranging from 1 mm to 30 mm; or
    e) the step interface is flexible; or
    f) the cannula is configured with a plurality of the step interfaces each of which constituting a mechanical vibration intensifier; or
    g) the main body radially protrudes from a first secondary body to define a first step interface, and said first secondary body radially protrudes from a second secondary body to define a second step interface.

7. The cannula according to claim 1, wherein the roughened surface is constituted by a plurality of irregularities that radially protrude from a smooth surface of the cannula body by a dimension of at least 20 microns, or by a plurality of longitudinally spaced rings that radially protrude from a smooth surface of the secondary body by a dimension of at least 20 microns.

8. The cannula according to claim 1, further comprising an additional PBPI configured as a resilient element fixed at one end which becomes plastically deformed in response to increased resistance provided by the proximal bone to indicate initial penetration thereinto.

9. The cannula according to claim 8, wherein the resilient element is an atraumatic helical compression spring made of, or coated with, biocompatible material and which is fit about the cannula body and provides an indication as to depth of penetration as a function of spring resistance.

10. The cannula according to claim 1, further comprising an additional PBPI configured as a frictionally engageable element by which a tactile indication of frictional engagement between said element and the cannula body and therefore of penetration into the proximal bone is transmittable to a health practitioner.

11. The cannula according to claim 1, wherein a distal end of the cannula body is configured with means for penetrating a bone cortex.

12. The cannula according to claim 3, wherein a longitudinal length of the roughened surface is at least a third of the longitudinal length of the secondary body.

13. The cannula according to claim 2, wherein the stopper is configured as a plurality of circumferentially spaced, radially expandable leaves, such that each leaf is defined by a longitudinal slit formed in the cannula body and is sufficiently long to undergo radial expansion when caused to contact the proximal bone cortex during the intraosseous injection.

14. The cannula according to claim 2, wherein the cannula body is a tubular body which comprises a main body and a secondary body distal to said main body, said main body being of a larger outer diameter than said secondary body, and wherein the stopper is configured with a plurality of circumferentially spaced integral scalpel blades protruding radially outwardly from said secondary body, each of said scalpel blades terminating with a sharpened and widened distal surface configured to contact the proximal bone cortex during the intraosseous injection.

15. The cannula according to claim 14, wherein each of the integral scalpel blades is made of metallic or plastic material.

16. A terminable intraosseous device, comprising:
   a) a penetrator for penetrating a bone cortex of a proximal bone;
   b) the cannula according to claim 3, which is configured with a lumen, wherein the secondary body is thin-walled body and proximal to said penetrator; and
   c) a reinforcing member insertable within said lumen for reinforcing the secondary body and connected to a component of the cannula,
   wherein an infusion fluid is flowable through said lumen to a bone marrow cavity without being occluded by said reinforcing member and said penetrator.

17. The device according to claim 16, wherein the penetrator is a needle element that is integrally formed with the secondary body and the reinforcing member is a truncated solid-core post inserted within the lumen of the secondary body.

18. The device according to claim 16, wherein the reinforcing member is an insert positioned within, and fixedly attached to a wall of, the lumen of the secondary body and the penetrator is a solid needle element which is integrally formed with said insert, and wherein one or more apertures are formed in both the secondary body and said insert to facilitate discharge of the infusion fluid into the bone marrow cavity.

19. A terminable intraosseous device adapted to indicate penetration into a cortex of a target bone, comprising
   a) a penetrator for penetrating a bone cortex of a proximal bone;
   b) said cannula body according to claim 3;
   c) a resilient element connected to said cannula body and configured to become plastically deformed and to cause a distance between said cannula body and said penetrator to become reduced in response to increased resistance provided by the proximal bone during initial penetration thereinto; and
   d) an additional PBPI, said additional PBPI comprising a visually indicative element which is concealed when the distance between said cannula body and said penetrator is a first distance and which is exposed when the distance between said cannula body and said penetrator is a second distance that is changed relative to the first distance.

20. The cannula according to claim 1, which is a side-tubulation cannula and is stabilized during performance of the intraosseous injection.

21. The device according to claim 19, wherein the penetrator and cannula body are prevented from being distally displaced when in a pre-penetration position.

22. The device according to claim 19, wherein the cannula body is related to a side-tubulation cannula.

* * * * *